United States Patent
de Dier et al.

(10) Patent No.: US 8,357,135 B2
(45) Date of Patent: Jan. 22, 2013

(54) METHOD OF MAKING DIAPER SIDE PANELS

(75) Inventors: Bart de Dier, Oud-Turnhout (BE); Ad van Hooijdonk, Vosselaar (BE)

(73) Assignee: Avery Dennison Corporation, Pasadena, CA (US)

( * ) Notice: Subject to any disclaimer, the term of this patent is extended or adjusted under 35 U.S.C. 154(b) by 123 days.

(21) Appl. No.: 12/092,087

(22) PCT Filed: Sep. 19, 2007

(86) PCT No.: PCT/US2007/078844
§ 371 (c)(1), (2), (4) Date: Apr. 30, 2008

(87) PCT Pub. No.: WO2008/036706
PCT Pub. Date: Mar. 27, 2008

(65) Prior Publication Data
US 2008/0262461 A1    Oct. 23, 2008

Related U.S. Application Data

(60) Provisional application No. 60/826,274, filed on Sep. 20, 2006.

(51) Int. Cl.
*A61F 13/56* (2006.01)
*B32B 37/14* (2006.01)
*B32B 37/22* (2006.01)

(52) U.S. Cl. .............. 604/385.04; 604/389; 604/390; 604/391; 156/270; 156/302

(58) Field of Classification Search .......... 604/389–391, 604/385.04, 385.01, 385.03; 156/269, 270, 156/302
See application file for complete search history.

(56) References Cited

U.S. PATENT DOCUMENTS

| | | | |
|---|---|---|---|
| 4,299,223 A * | 11/1981 | Cronkrite | 604/390 |
| 5,312,387 A | 5/1994 | Rossini et al. | |
| 5,399,219 A | 3/1995 | Roessler et al. | |
| D368,775 S | 4/1996 | Gobran | |
| D372,532 S | 8/1996 | Rossini et al. | |
| 5,580,411 A | 12/1996 | Nease et al. | |
| D377,979 S | 2/1997 | Plaschko et al. | |

(Continued)

FOREIGN PATENT DOCUMENTS

| | | |
|---|---|---|
| EP | 0379850 | 12/1989 |
| EP | 1452158 | 9/2004 |

(Continued)

OTHER PUBLICATIONS

PCT/US2007/078844; PCT International Search Report dated Dec. 5, 2007.

*Primary Examiner* — Katarzyna Wyrozebski Lee
*Assistant Examiner* — Scott W Dodds
(74) *Attorney, Agent, or Firm* — Avery Dennison Corporation

(57) ABSTRACT

A method of making a plurality of diaper side panels (10, 12) from a continuous strip (40). The strip (40) comprises a central region (42), a first lateral region (44), a second lateral region (46), a first set of fasteners (36) anchored to the first lateral region (44), and a second set of fasteners (38) anchored to the second lateral region (46). The strip (40) is separated in the machine direction (M) to form a first set of the side panels (10) and a second set of the side panels (12), so that the side panels (10) each include a fastener (36) from the first set and the side panels (12) each include a fastener (38) from the second set.

10 Claims, 21 Drawing Sheets

U.S. PATENT DOCUMENTS

| | | |
|---|---|---|
| 5,603,708 A | 2/1997 | Seth |
| 5,620,780 A * | 4/1997 | Krueger et al. ............... 428/179 |
| D384,151 S | 9/1997 | Raufman |
| D384,152 S | 9/1997 | Raufman |
| 5,705,013 A | 1/1998 | Nease et al. |
| 5,759,317 A | 6/1998 | Justmann |
| 5,876,531 A | 3/1999 | Jacobs et al. |
| D421,802 S | 3/2000 | Van Gompel et al. |
| D422,077 S | 3/2000 | Suprise et al. |
| D422,078 S | 3/2000 | Vukos et al. |
| 6,051,094 A | 4/2000 | Melbye et al. |
| D427,677 S | 7/2000 | Bruemmer-Prestley |
| D428,143 S | 7/2000 | Schmoker et al. |
| D428,144 S | 7/2000 | Bruemmer-Prestley et al. |
| D428,145 S | 7/2000 | Bruemmer-Prestley et al. |
| D435,103 S | 12/2000 | Schmoker et al. |
| 6,171,432 B1 | 1/2001 | Brisebois et al. |
| 6,241,716 B1 * | 6/2001 | Ronnberg .................... 604/391 |
| 6,267,836 B1 | 7/2001 | Fenske et al. |
| D448,079 S | 9/2001 | Bruemmer-Prestley et al. |
| D456,508 S | 4/2002 | Schroeder et al. |
| D457,951 S | 5/2002 | Abney et al. |
| 6,514,233 B1 | 2/2003 | Glaug |
| D472,314 S | 3/2003 | Wu |
| 6,652,696 B2 | 11/2003 | Kuen et al. |
| D486,230 S | 2/2004 | Swenson et al. |
| D486,231 S | 2/2004 | Kielb et al. |
| D486,577 S | 2/2004 | Swenson et al. |
| D489,450 S | 5/2004 | Wu et al. |
| D498,843 S | 11/2004 | Kielb et al. |
| 6,979,380 B2 | 12/2005 | Thorson et al. |
| 7,070,672 B2 * | 7/2006 | Alcantara et al. ............. 156/265 |
| 2004/0016499 A1 | 1/2004 | Miyamoto et al. |
| 2005/0072512 A1 | 4/2005 | Shiomi et al. |
| 2005/0256495 A1 * | 11/2005 | Schlinz et al. ......... 604/385.201 |
| 2005/0273072 A1 * | 12/2005 | Hird et al. ................ 604/385.24 |
| 2006/0201619 A1 | 9/2006 | Andrews |

FOREIGN PATENT DOCUMENTS

| | | |
|---|---|---|
| EP | 1731122 | 12/2006 |
| WO | 9007426 | 7/1990 |
| WO | 2005110314 | 11/2005 |

* cited by examiner

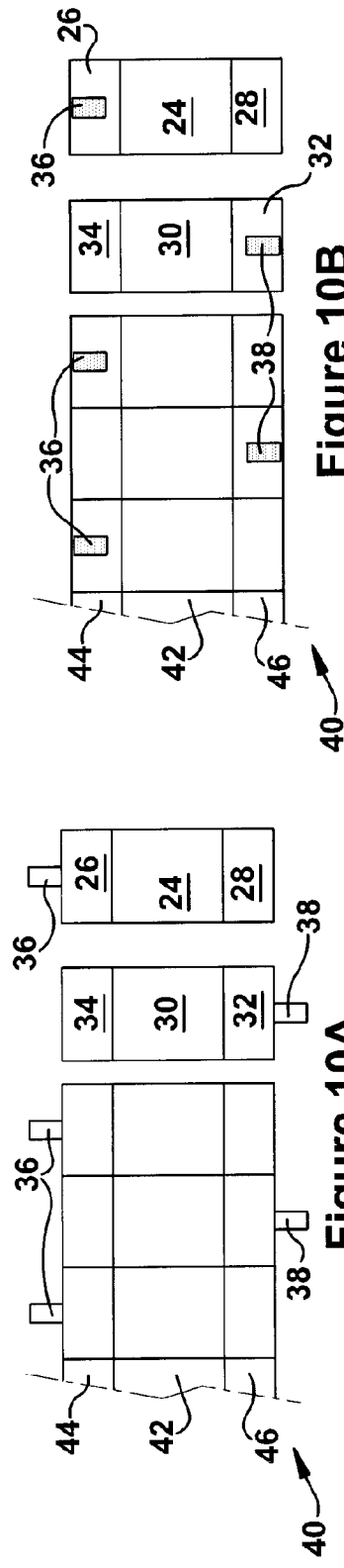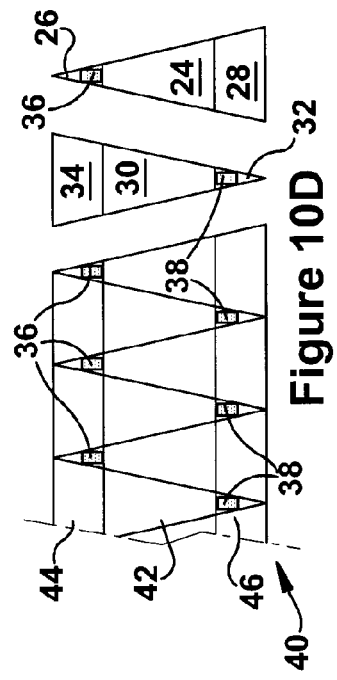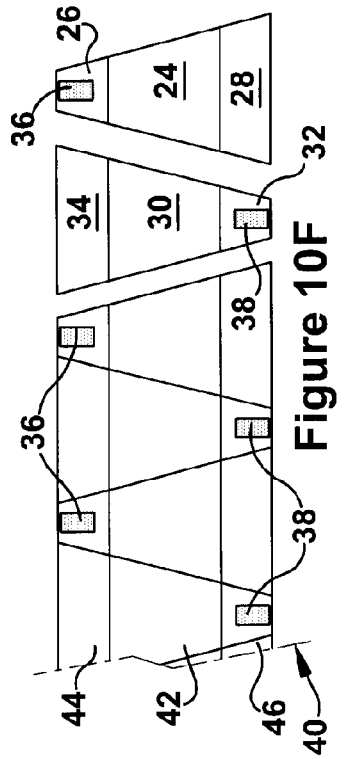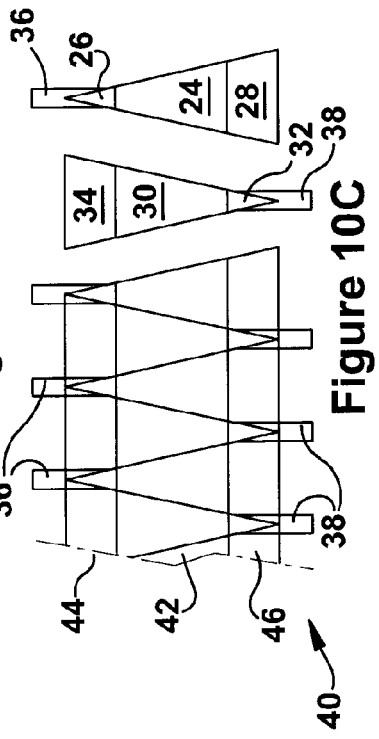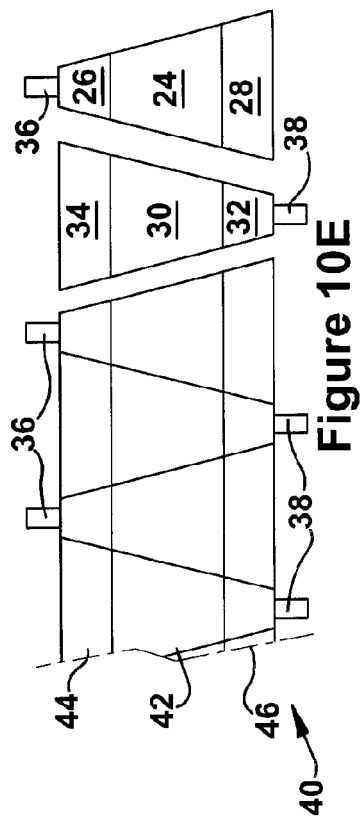

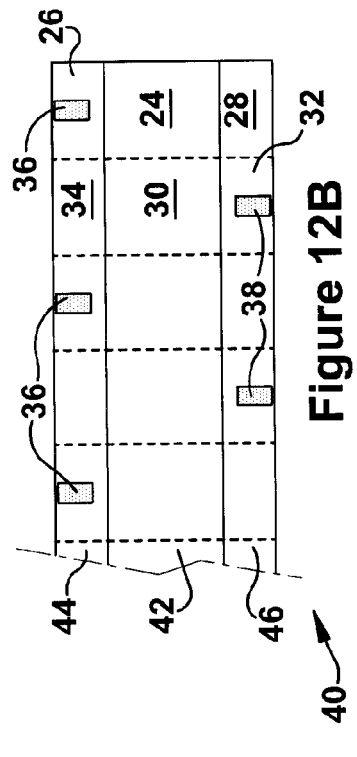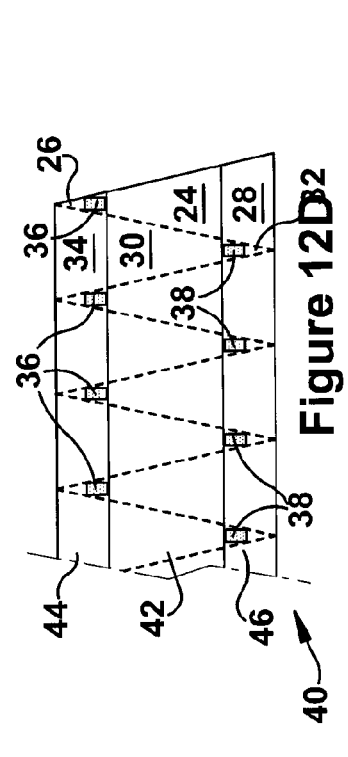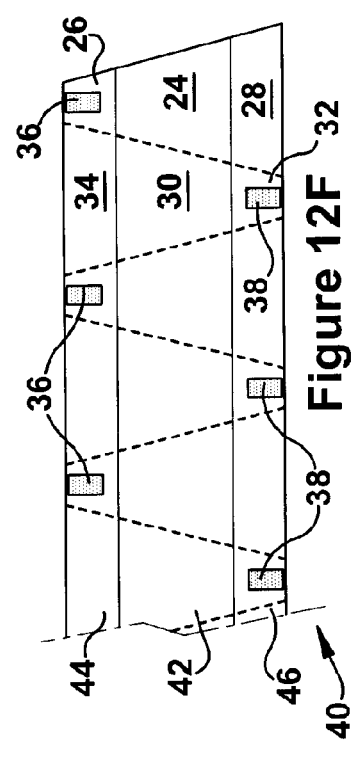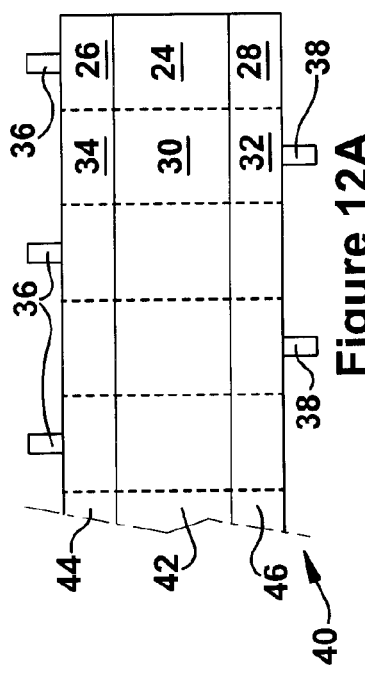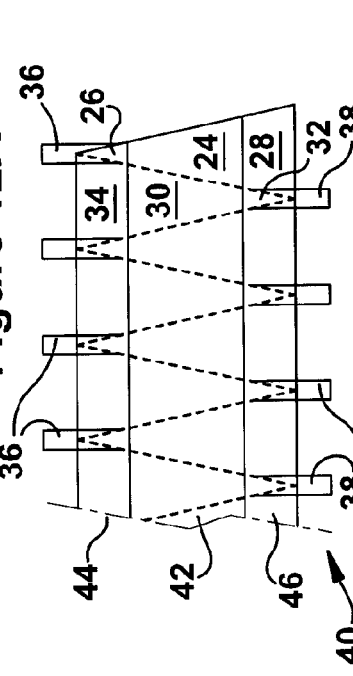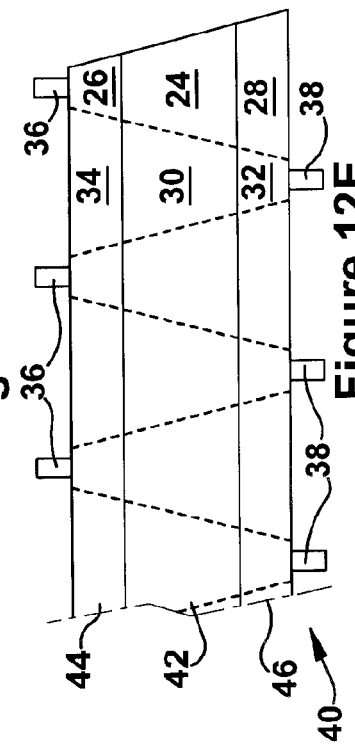

METHOD OF MAKING DIAPER SIDE PANELS

This application is a national phase of International Application No. PCT/US2007/078844, filed Sep. 19, 2007, which claims priority to U.S. Provisional Application Ser. No. 60/826,274 filed Sep. 20, 2006. The entire disclosure of this international application and the entire disclosure of this provisional application are hereby incorporated by reference.

A diaper can comprise chassis, a side panel secured to a left side of the rear portion of the chassis, and another side panel secured to the right side of the rear portion of the chassis. The side panels typically have the same construction and the left side panel and the right side panel are positioned symmetrically relative to the diaper chassis. Each side panel can include a fastening section carrying a fastener for selectively fastening to the front portion of the chassis (or an extension therefrom) during use of the diaper.

SUMMARY

A method of making side panels is provided wherein a continuous strip is separated into a first set of side panels and a second set of side panels. The side panels in the first set each include a securement section for securing it to the left side of a diaper chassis and a fastening section carrying a first fastener. The side panels in the second set each include a securement section for securing it to the right side of the diaper chassis and a fastening section, carrying a second fastener. The continuous strip is constructed, and the panel-separating steps are performed, so that waste panel material is eliminated and fastening material minimized.

DRAWINGS

FIGS. 10A-10J are schematic views of some possible methods for making side panels from the continuous strip.

FIGS. 12A-12J are plan views of possible continuous strips wherein partial separations have been provided.

DESCRIPTION

Figure 1A:
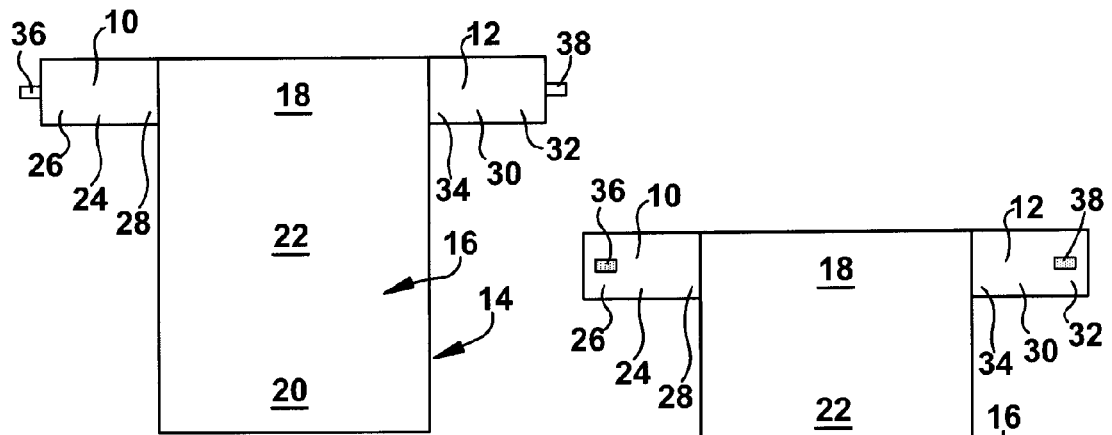
FIGS. 1A-1J are plan views of possible diapers, each having a side panel secured to a left side of its chassis and another side panel secured to the right side of its chassis.
Figure 1B:
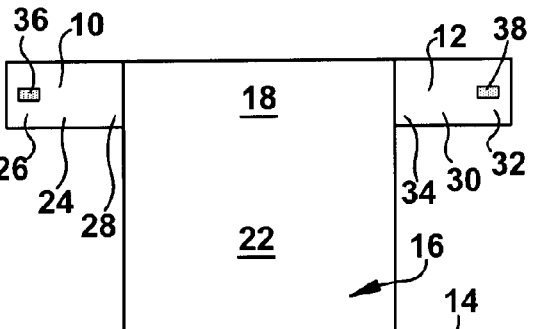
Figure 1C:
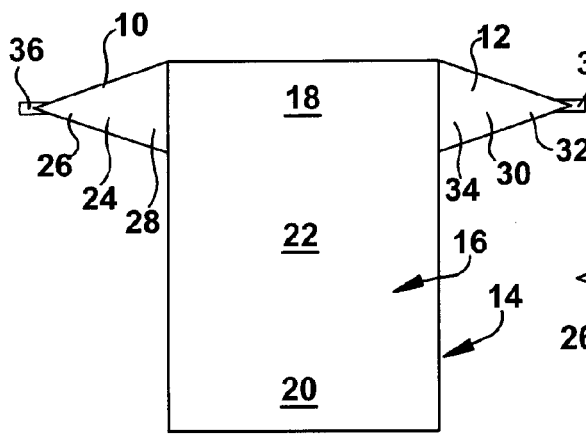
Figure 1D:
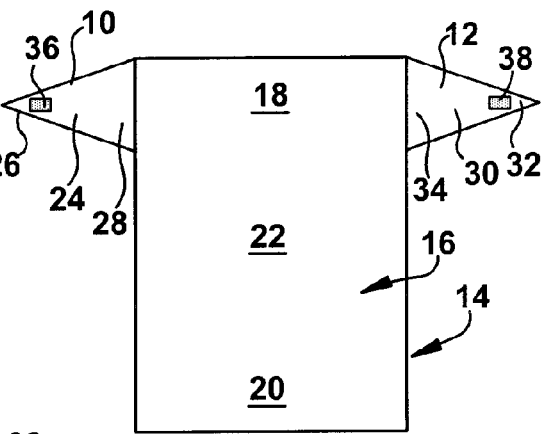
Figure 1E:
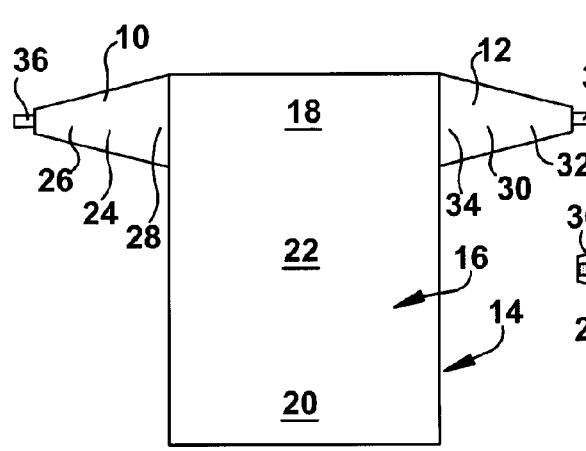
Figure 1F:
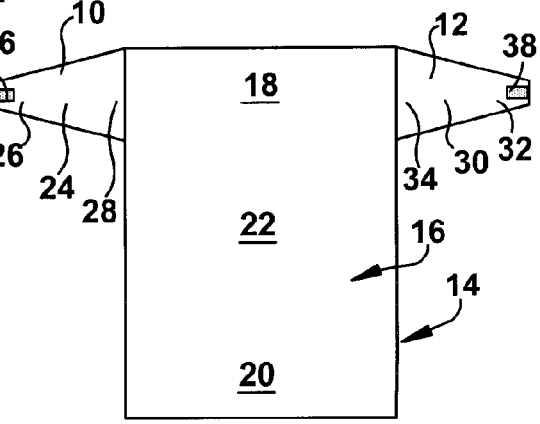
Figure 1G:
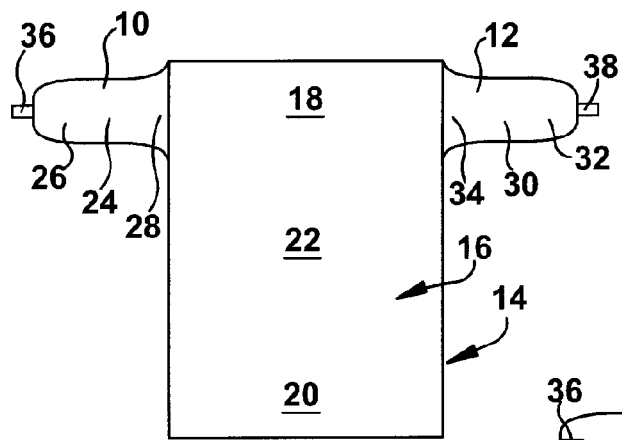
Figure 1H:
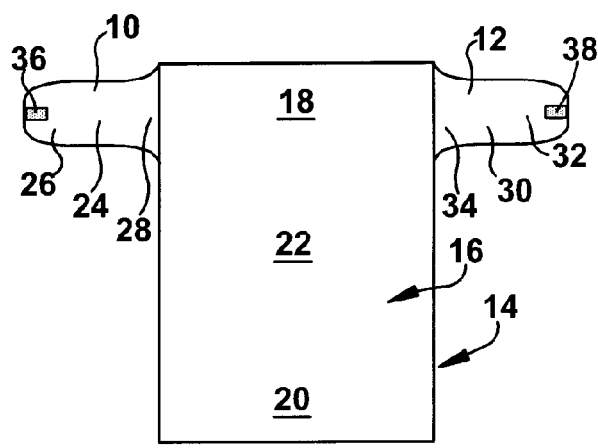
Figure 1I:
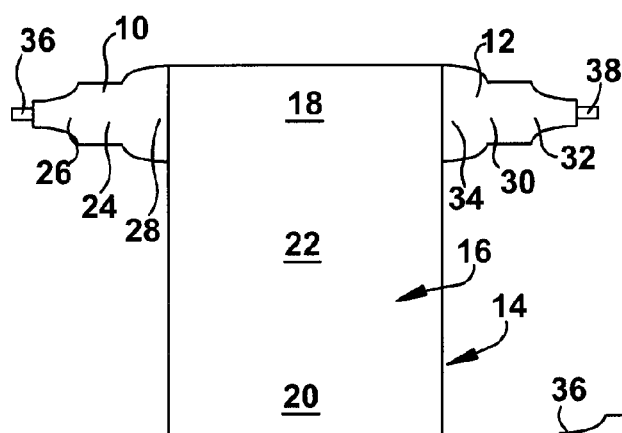
Figure 1J:
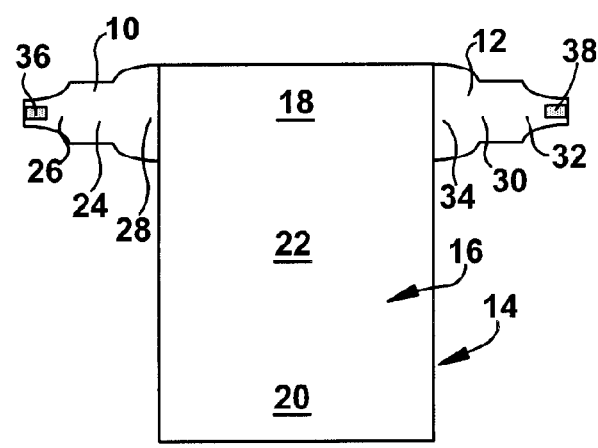

Referring now to the drawings, and initially to FIGS. 1A-1J, a first side panel 10 and a second side panel 12 are shown secured to a diaper 14 and, more particularly, secured to its chassis 16. The diaper chassis 16 can include a liquid permeable topsheet, a liquid impermeable backsheet, and an absorbent core interposed therebetween. The diaper 14 can be made, for example, in smaller sizes for a baby or child, and/or in larger sizes for an adult. The term "diaper" as used in this specification is intended to cover a disposable absorbent article, that is an article that is designed to be used until soiled and then discarded, rather than being washed and used again.

The chassis 16 can comprise a rear portion 18, a front portion 20, and a crotch portion 22. In the illustrated embodiment, the side panel 10 is secured to the left-hand side of the chassis rear portion 18 and the side panel 12 is secured to the right-hand side of the chassis rear portion 18. That being said, other side-panel-securement sites are certainly possible and contemplated. For example, side panels 10/12 could additionally or alternatively be secured to the left/right sides of the front chassis portion 20.

The first side panel 10 can be viewed as having a central section 24, a fastening section 26, and a securement section 28; the second side panel 12 can likewise be viewed as having a central section 30, a fastening section 32, and a securement section 34. The fastening sections 26/32 are adapted to be selectively fastened to a surface during use of the diaper 14. The fastening section 26 includes a first fastener 36 and the fastening section 32 includes a second fastener 38. The fasteners 36/38 can be used to fasten the fastening sections 26/32 to the front chassis portion 20 or to extensions (e.g., ears, additional panels, etc.) projecting outward from the front chassis portion 20.

The securement sections 28/34 are secured to the left/right sides of the chassis rear portion 18. Usually (but not necessarily), the sections 28/38 are permanently secured chassis 16 whereby they are not selectively removable therefrom during diaper use.

Referring now to FIGS. 2A-2D, possible constructions for a continuous strip 40 for making a plurality of the side panels 10/12 are shown. The continuous strip 40 comprises a central region 42, a first lateral region 44, and a second lateral region 46. The regions 42/44/46 each run the length of strip 40 in the machine direction M, with the first lateral region 44 being located on one longitudinal side of the central region 42 and the second lateral region 46 being located on the other longitudinal side of the central region 42.

The distal longitudinal edge of the first lateral region 44 and the distal longitudinal edge of the second lateral region 46 define the width (w) of the strip 40 in the cross direction C. The first lateral region 44 and the second lateral region 46 can have substantially the same width in the cross direction C and/or mirror each other relative to the central region 42. In this manner, as is explained in more detail below, the first side panel 10 will have the same construction as the second side panel 12.

A first set of fasteners 36 are anchored to the first lateral region 44, and a second set of fasteners 38 are anchored to the second lateral region 46. The first set of fasteners 36 are spaced (e.g., evenly spaced) from each other in the machine direction M (i.e., they are separated from each other and do not constitute a continuous part of the strip 40). The second set of fasteners 38 are likewise spaced (e.g., evenly spaced) from each other in the machine direction M. The fasteners 36 and the fasteners 38 can be staggered in the cross direction C so that a fastener 36 will not be positioned parallel with a fastener 38 even though the inter-fastener spacing will be the same for both sets of fasteners 36/38. The fasteners 36 can have the same construction as the fasteners 38 and/or can be symmetrically positioned relative to each other.

As is best seen by referring briefly back to the 1$^{st}$ series of drawings, the central region 42 forms the central section 24 of the first side panel 10 and the central section 30 of the second side panel 12. The first lateral region 44 forms the fastening section 26 of the first side panel 10 and the securement section 34 of the second side panel 12. The second lateral region 46 forms the securement section 28 of the first side panel 10 and the fastening section 32 of the second side panel 12. This corresponds to the fastener 36 being anchored to the fastening section 26 of the first side panel 10 and the fastener 38 being anchored to the fastening section 32 of the second side panel 12. Fasteners 36/38 do not occupy the securement sections 28/34 of the panels 10/12.

Figure 2A:
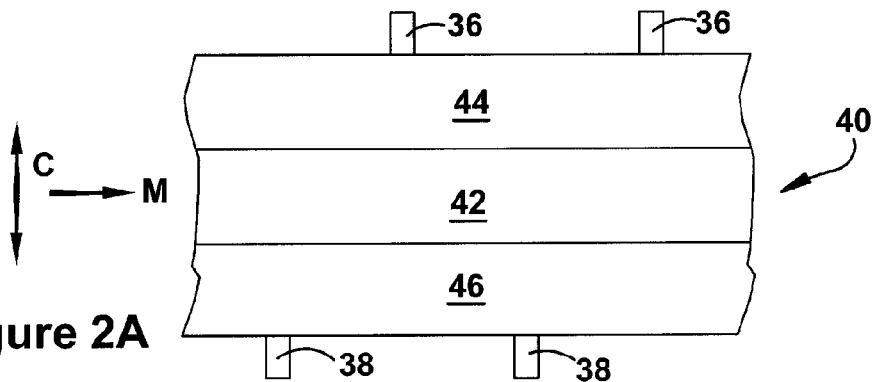
FIGS. 2A-2D are plan views of some possible continuous strips for making the side panels.
Figure 2B:
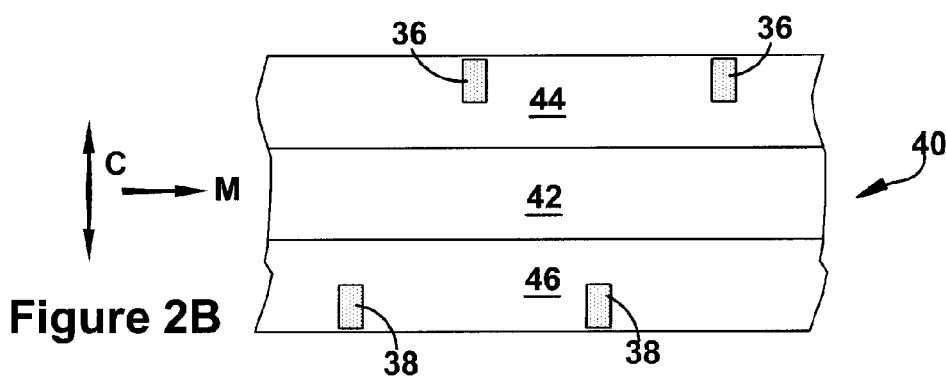

Returning now to FIGS. 2A-2D, the central region 42 can be made of a different material, and/or have different properties, than the lateral regions 44/46. (FIGS. 2A and 2B.) For example, the central region 40 can be elastic and the lateral regions 44/46 can be nonelastic. The central elastic region 42 can occupy between 20% to 90% of the width of the strip 40 in the cross direction C, with the lateral regions 44/46 occupying the remaining territory on either side thereof. A physical line of demarcation between the regions 42/44/46 (e.g., a seam, joint, weld, layer step, material manipulation zones, etc.) will usually be present.

Figure 2C:
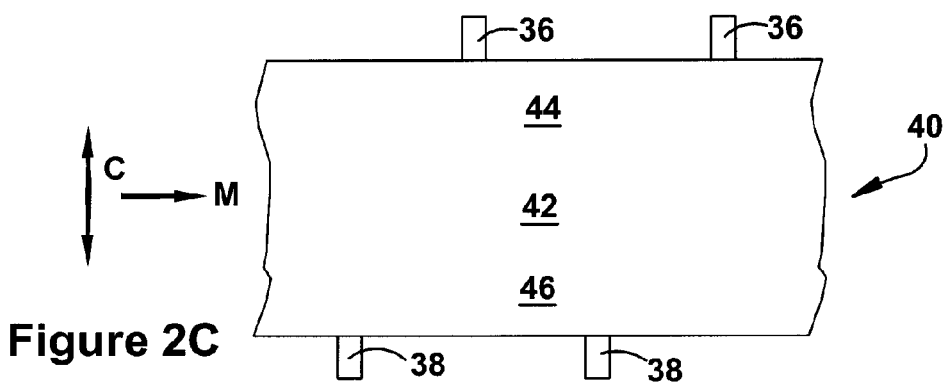
Figure 2D:
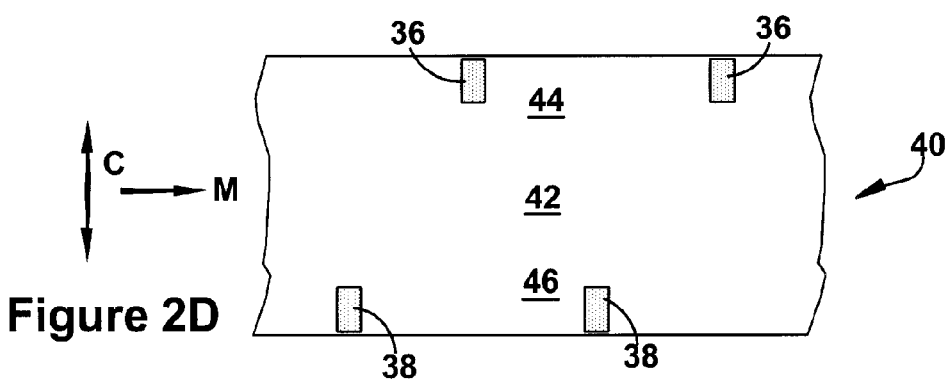

Alternatively, the central region 42 can be made of the same material, and/or have the same properties, than the lateral regions 44/46. (FIGS. 2C and 2D.) For example, the regions 42/44/46 can all be inelastic or the regions 42/44/46 can all be elastic. In the latter two scenarios, the strip 40 can have a continuous structure in the cross direction C as opposed to, for example, a structure having seams, joints, layer steps, material manipulation zones, etc.

An elastic central region 42 and/or elastic lateral regions 44/46 can comprise an elastic nonwoven fabric and/or an elastic film laminate. With particular reference to an elastic film laminate, it can comprise, for example, an elastic film layer with an elastic fabric layer on one or both sides. Additionally or alternatively, an elastic region can comprise a laminate of elastic and nonelastic layers, with the nonelastic layer(s) being activated to render them elastic. For example, an elastic region 42/44/46 can comprise an elastic layer sandwiched between two nonelastic layers (e.g., nonelastic nonwoven layers), with the nonelastic layers being activated.

A nonelastic central region 42 and/or nonelastic lateral regions 44/46 can comprise a nonelastic fabric, such a nonwoven nonelastic fabric. When the central region 42 differs in elasticity properties from the lateral regions 44/46, each region 42/44/46 can comprise an elastic material with the relevant regions (e.g., the lateral regions 44/46) being manipulated to render them nonelastic. Likewise, each region 42/44/46 can comprise a nonelastic material with the relevant region(s) (e.g., the central region 42) being manipulated to render them elastic. It may be further noted that different degrees of material manipulation can be used on the central region 42 as opposed to the lateral regions 44/46 to provide differing elasticity or other properties. Additionally or alternatively, a nonelastic regions 42/44/46 can be laminate comprising, for example, a pair of nonelastic layers (e.g., nonelastic nonwoven fabric) with or without a structural layer sandwiched therebetween.

Figure 3A:
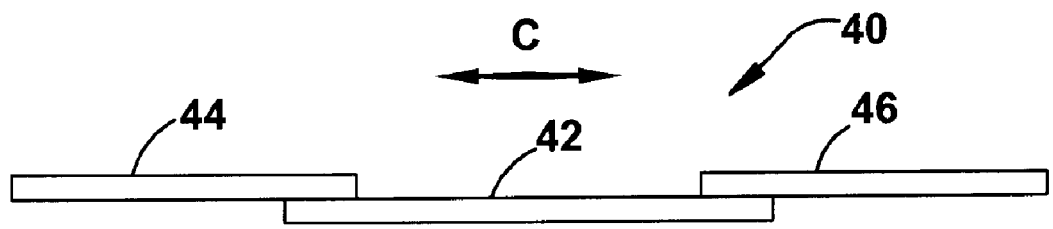
FIGS. 3A-3D are side views of some possible layer arrangements for the continuous strip.
Figure 3B:
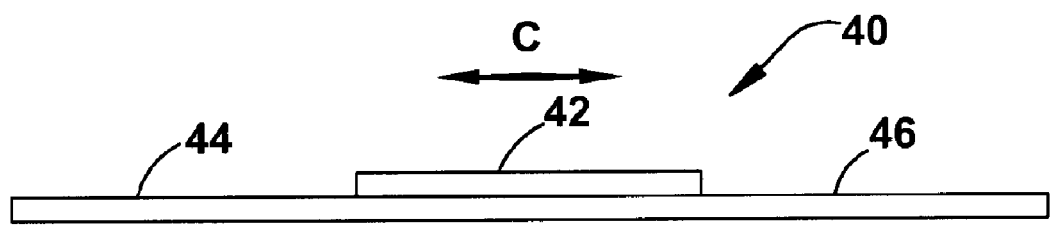
Figure 3C:
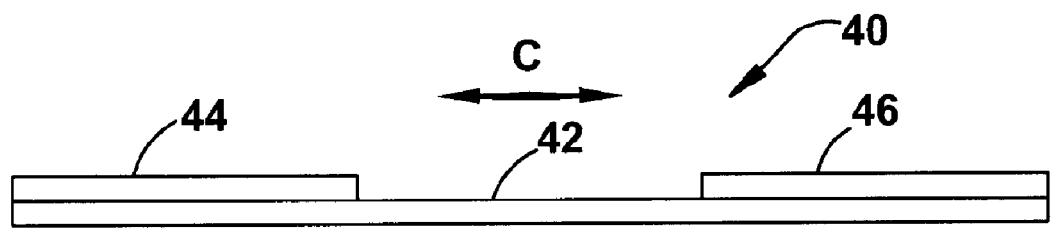
Figure 3D:
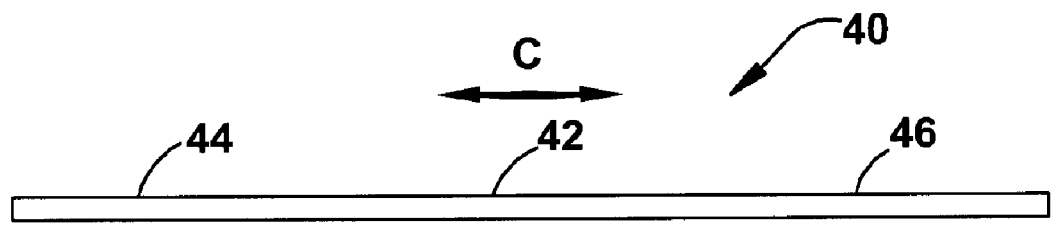

In either or any event, the continuous strip 40 can comprise one or more layers non-coextensive across the central region, the first lateral region, and the second lateral region one. (FIGS. 3A-3C.) Additionally or alternatively, the continuous strip 40 can comprise one or more layers coextensive across the central region 42, the first lateral region 44, and the second lateral region 46. (FIGS. 3B-3D.) Furthermore, as indicated above, material manipulation can be performed on some or all of the coextensive layers and/or noncoextensive layers.

Constructions wherein first lateral region 44 and the second lateral region 46 are made of different materials and/or have different properties is certainly possible. However, such a construction will not result in the side panel 10 and the side panel 12 being of the same construction. Specifically, for example, although the center sections 24/30 would be the same in each side panel 10/12. the fastening sections 26/32 would have different constructions and the securement sections 28/34 would have different constructions.

Figure 4A:
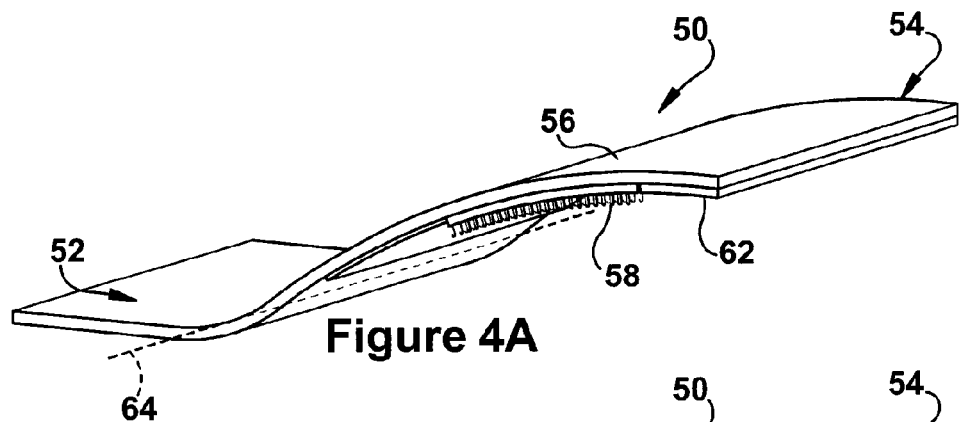
FIGS. 4A-4E are close-up views of some possible fastener constructions.
Figure 4B:
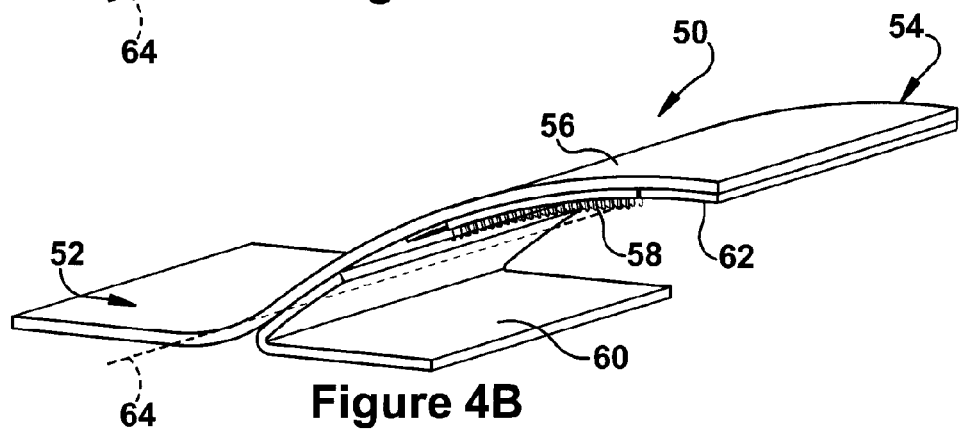
Figure 4C:
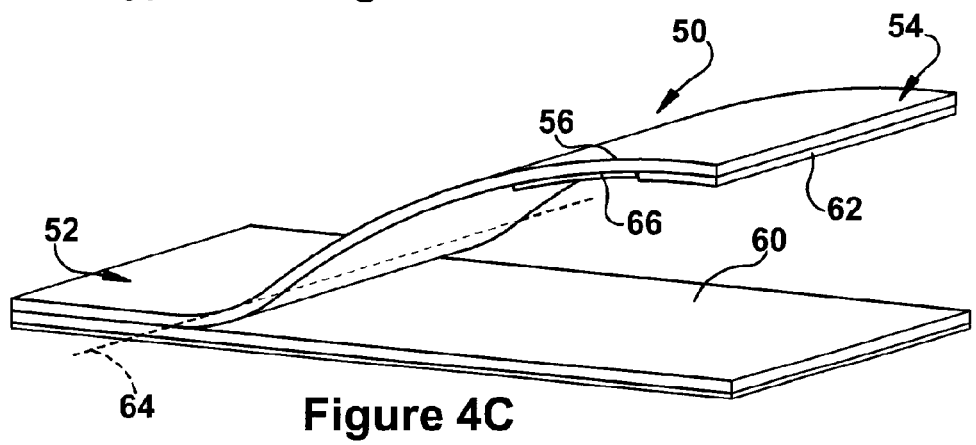

As is shown in FIGS. 2A and 2C, the fasteners 36/38 can be anchored to the longitudinal edge of the respective lateral region 44/46. Specifically, for example, the fasteners 36/38 can each comprise a tape assembly 50 having an end 52 anchored to the respective lateral region 44/46 and an opposite end 54 adapted for selective fastening to the diaper chassis portion 16. The tape assembly 50 can comprise a fastening tape 56 (carrying fastening means 58 such as hook elements), a release tape 60, and/or a fingerlift 62. (FIGS. 4A-4C.) A fold 64 can be provided so that the tape assembly 50 can be folded to straddle both sides of the respective lateral region 44/46. The tape assembly 50 can additionally or alternatively comprise an adhesive area 66 as part of the fastening means 58 and/or as means to hold a used diaper in a bundle for disposal. (FIG. 4C.)

Figure 4D:
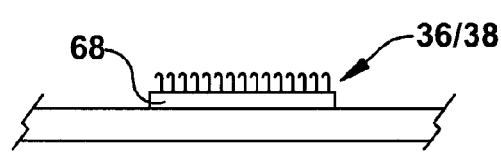
Figure 4E:
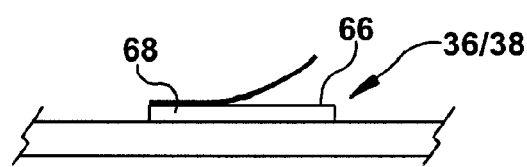

Instead of the fasteners 36/38 can be anchored to the longitudinal edge of the respective lateral region 44/46, the fastener 36/38 (and/or the fastening means 58) can instead be discrete areas 68 directly anchored to the region 44/46. (FIGS. 4D and 4E.) The fasteners 36/38 can be situated inboard from the longitudinal edge of the respective region 44/46 and/or the discrete areas 68 can comprise, for example, hook islands or adhesive patches. In either or any case, the use of discrete areas (e.g., islands or patches), instead of hook/adhesive rows which extend continuously in the machine direction M, results in a minimization of fastener-related material costs and, in some case, may facilitate side-panel-separation steps.

Figure 5A:
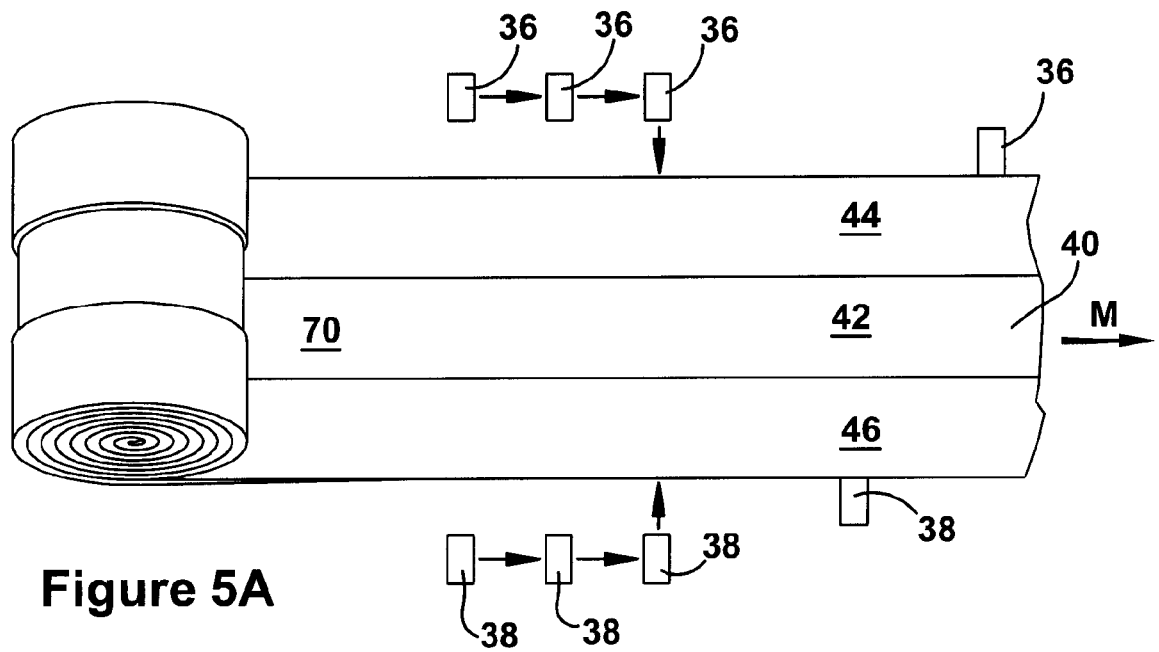
FIGS. 5A-5F are schematic views of some possible methods for making the continuous strip.
Figure 5B:
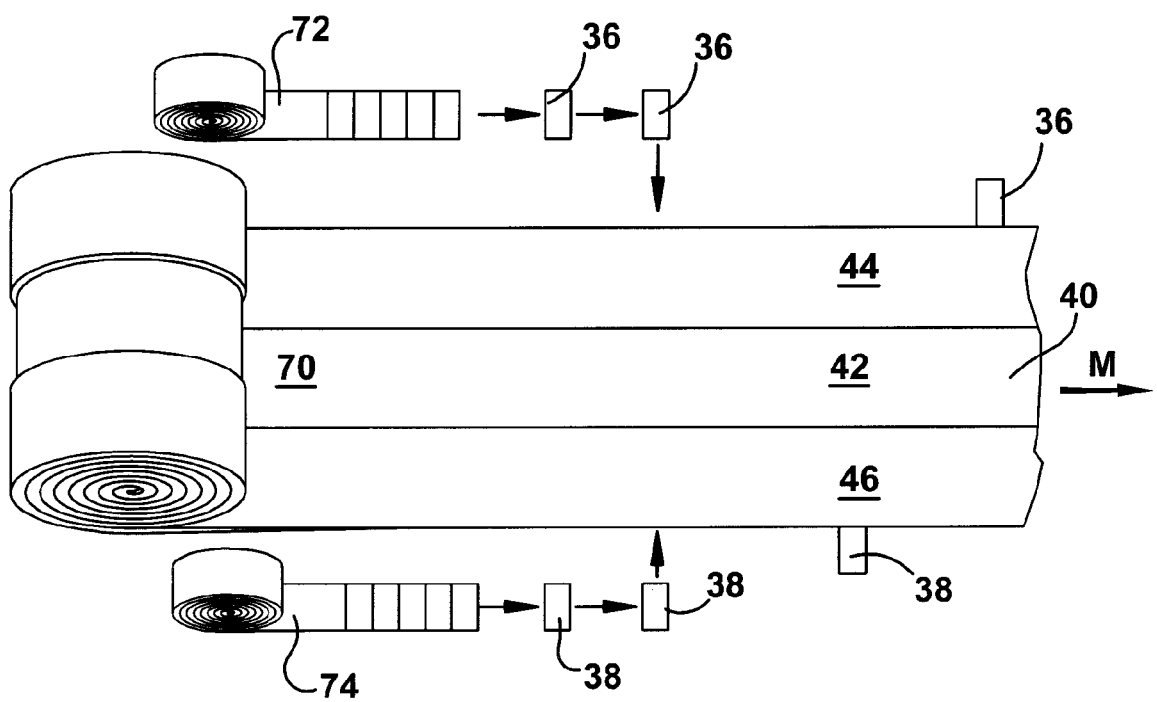
Figure 5C:
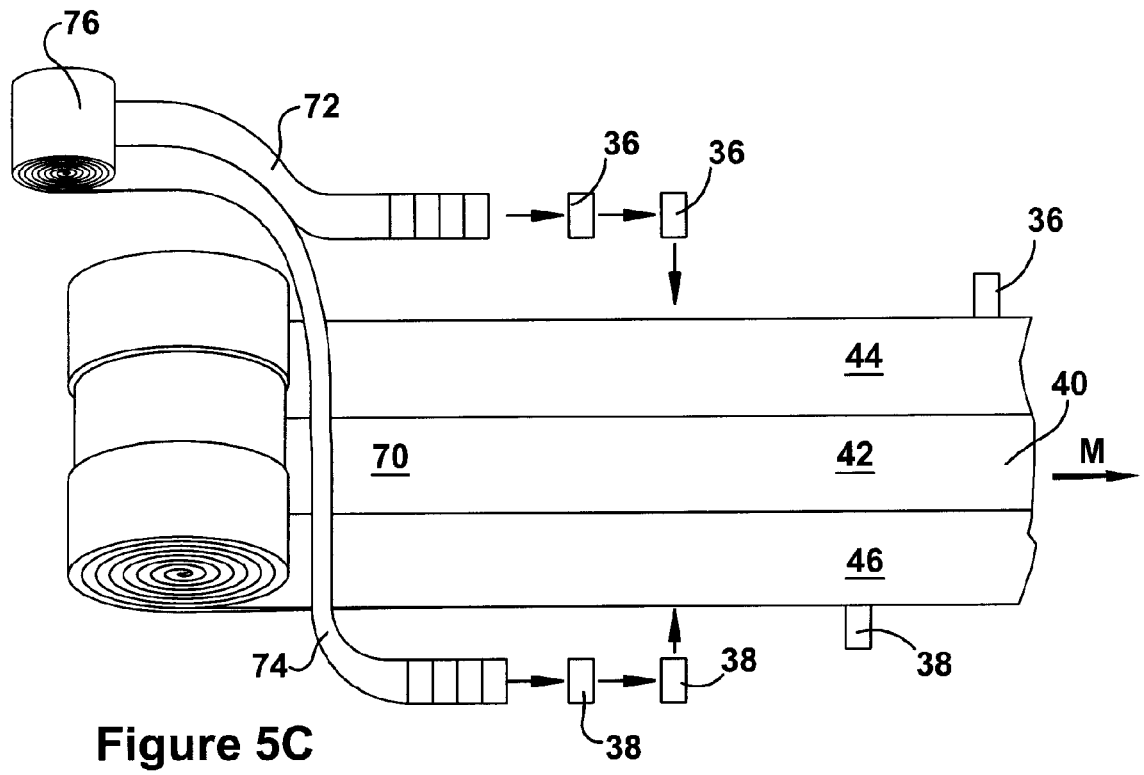
Figure 5D:
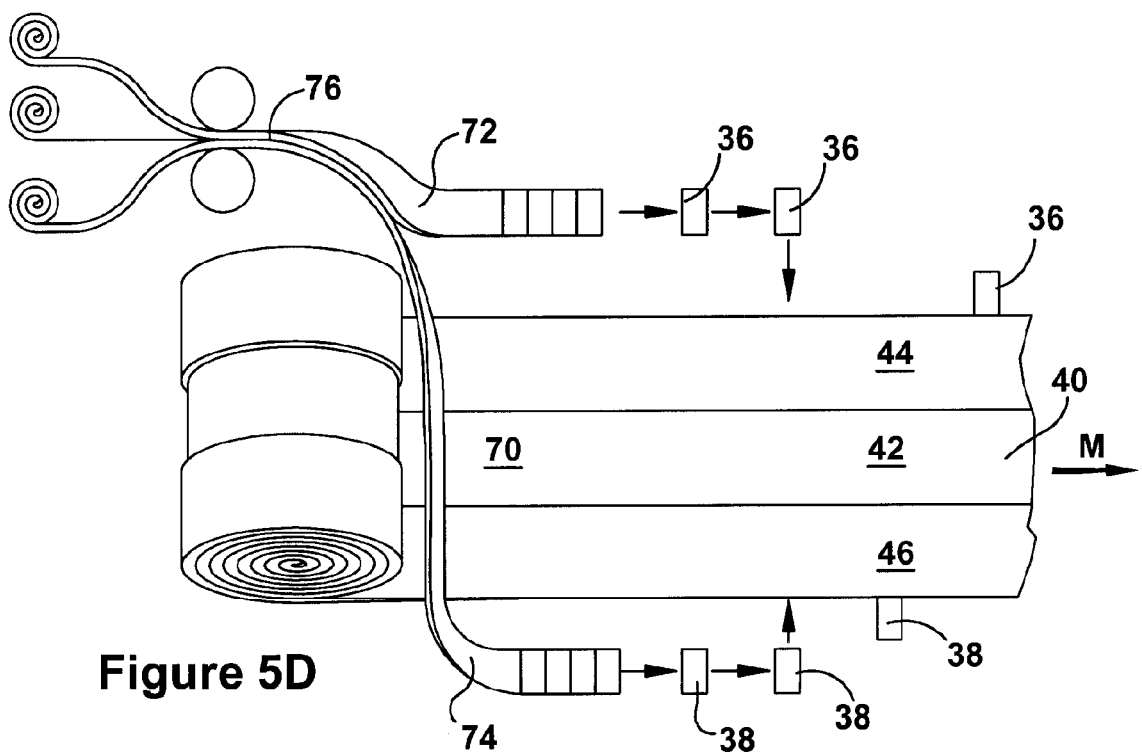
Figure 5E:
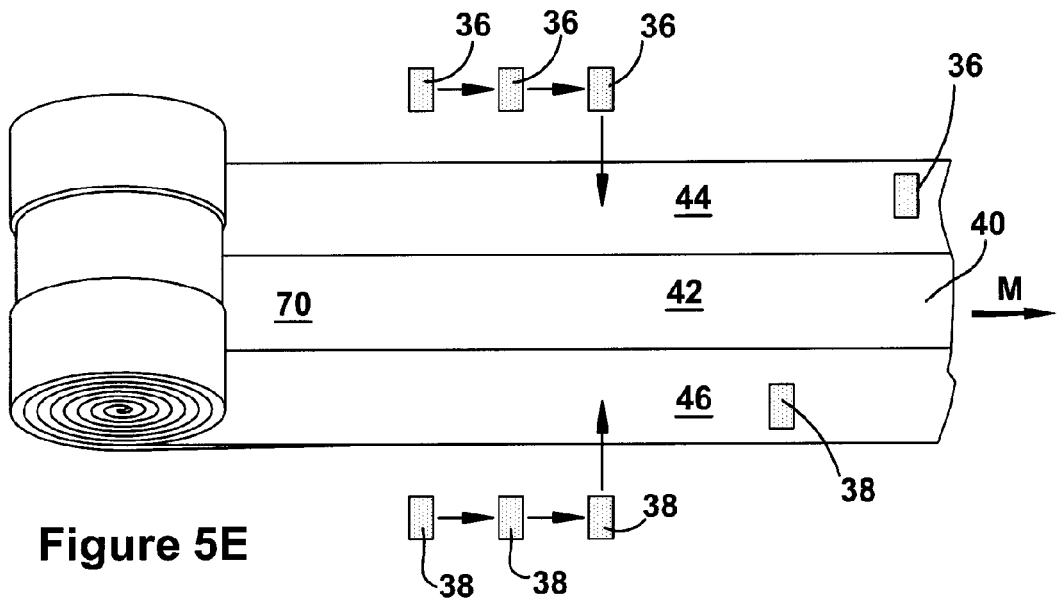
Figure 5F:
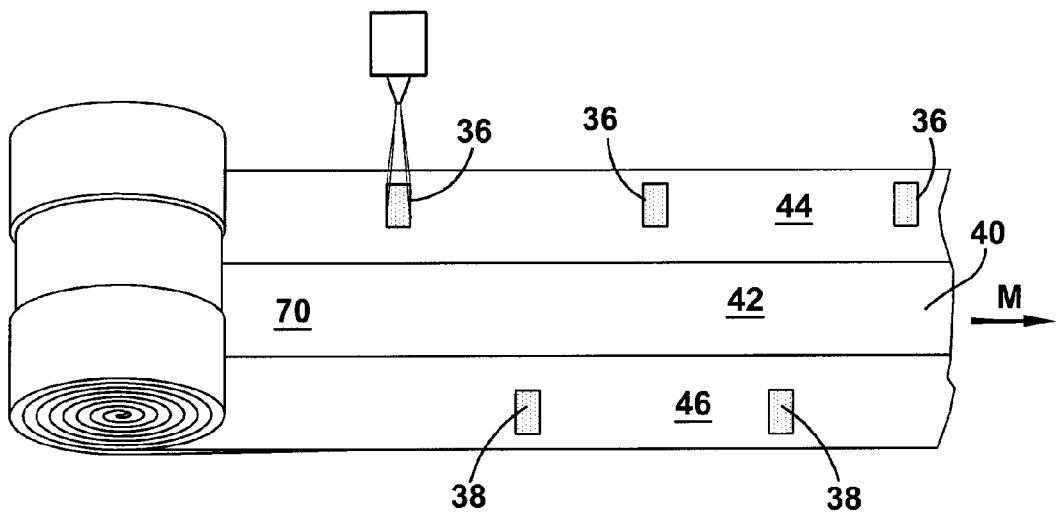

Possible methods for making the continuous strip 40s are shown schematically in FIGS. 5A-5F. This method generally comprises the steps of providing a web 70 of panel material (which includes the central region 42, the first lateral region 44, and the second lateral region 46), supplying the first set of fasteners 36, supplying the second set of fasteners 38, anchoring fasteners 36 to the first lateral region 44; and anchoring fasteners 38 to the second lateral region 46. (FIGS. 5A, 5E, and 5F.)

The web 70 of panel material can be provided in a format suitable for continuous supply, such as a roll. It may be possible for panel-material-formation steps to be performed in-line with the supplying and anchoring steps. However, if the production speed of panel material is significantly slower/faster than the production and/or supply speed of fastener-material, such in-line performance may not be effective. Also, in many cases, industry conventions will push towards the production of the web 70 of panel material (or panel stock material 78, introduced below) occurring at a location remote from the location whereat the fasteners 36/38 are supplied and anchored thereto.

The anchoring steps can comprise, for example, adhesive, heat, and/or ultrasonic bonding of the fasteners 36/38 to the lateral regions 44/46. If the fasteners 36/38 are tape assemblies, such as is shown in FIG. 5A, the fastener-supplying steps can comprise dividing a first ribbon 72 of fastener material in the machine direction M into the first fasteners 36 and dividing a second ribbon 74 of fastener material in the machine direction M into the second fasteners 38. (FIG. 5B.) The divisions can be cuts extending in the cross direction C which are substantially perpendicular in the machine direction M (as illustrated), or which are substantially nonparallel in the machine direction M.

Ribbon-formation can occur in-line with the supplying, dividing and/or anchoring steps. Specifically, for example, fastener stock 76 can be split in the cross direction C to produce the first ribbon 72 and the second ribbon 74. (FIG. 5C.) Additionally or alternatively, lamination of the tape layers can occur in-line with, and/or upstream from, the splitting, dividing, supplying, and/or anchoring steps to produce the ribbons 72/74 or the stock 76. (FIG. 5D.)

If the fasteners 36/38 are hook islands, they can be divided from ribbons (or another continuous supply format) and directly anchored to the web 70 in a similar manner as the tape fasteners. (FIG. 5E.) If the fasteners 36/38 are adhesive patches, they can be directly anchored to the relevant lateral region 44/46 by, for example, extrusion, printing, spraying and/or coating. (FIG. 5F.)

Figure 6A:
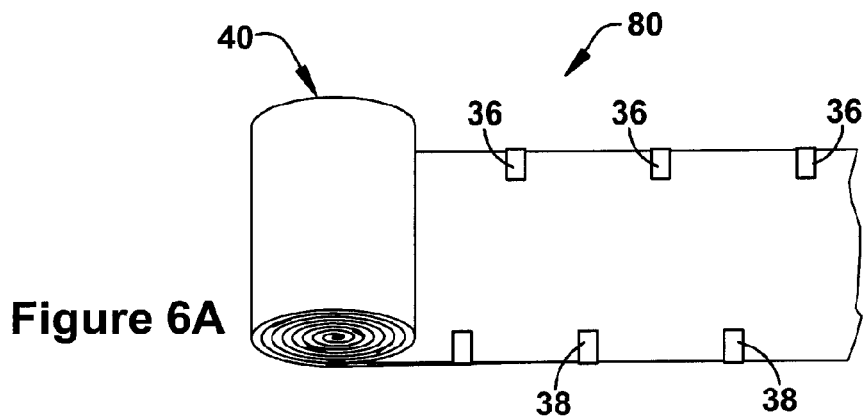
FIGS. 6A-6D are schematic views of some possible formats for continuous supply of the strip.
Figure 6B:
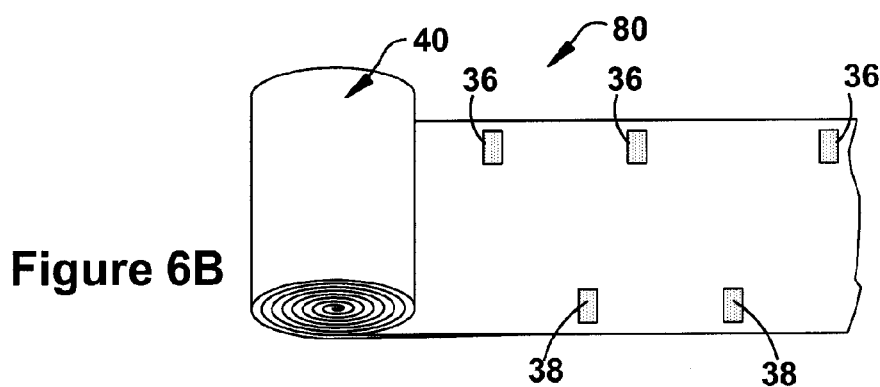
Figure 6C:
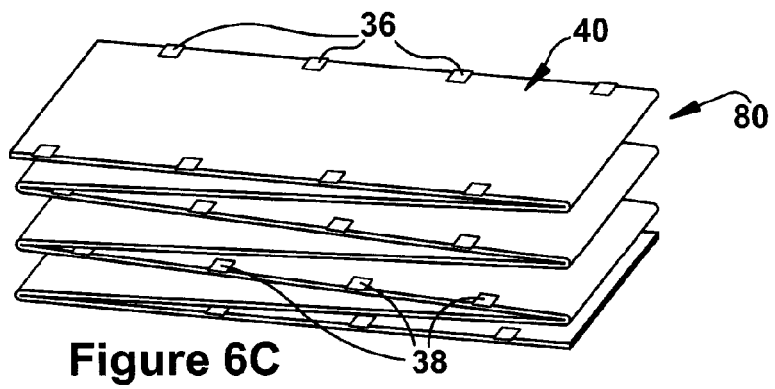
Figure 6D:
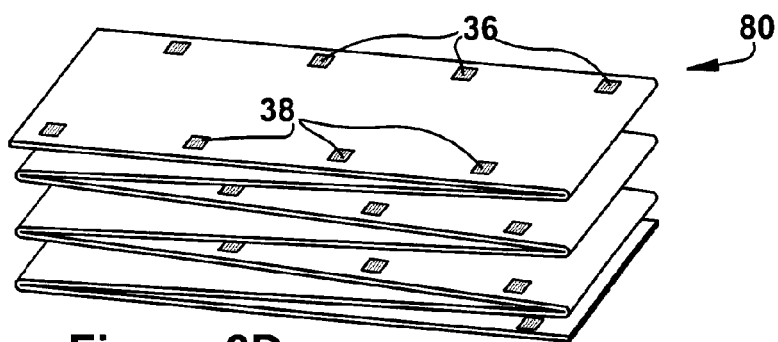

The completed strip 40 can be assembled into a format 80 suitable for continuous supply during subsequent panel-separation steps. For example, the strip 40 can be assembled into a roll (FIGS. 6A and 6B) or a festooned stack (FIGS. 6C and 6D). With particular reference to the tape fasteners 36/38, they can be folded to straddle the edges of the respective lateral regions 44/46. This folding-straddling step could be performed in-line with fastener-anchoring steps. With particular reference to the island/patch fasteners 36/38, measures may be necessary to prevent sticking, catching, or blocking between hooks/adhesive and adjacent surfaces and these measures could be performed in-line with the fastener-anchoring steps. In either or any event, assembling the strip 40 in such a format may not be necessary if panel-separation steps are performed in-line with strip-making steps and/or at the same location as the fastener-anchoring steps.

Referring now to FIGS. 7A-7E, some possible methods for making a plural number (n) of continuous strips 40 are shown. In these methods, panel stock material 78 is provided, split into the plural number (n) of webs 70 of panel material, the webs 70 are spread apart, and then the fasteners 36/38 are anchored to the lateral regions 44/46 of each web 70 of panel material. In the illustrated embodiment, the plural number (n) is three, whereby there are three webs 70 of panel material, three sets of first fasteners 36 and three sets of second fasteners 38.

Figure 7A:
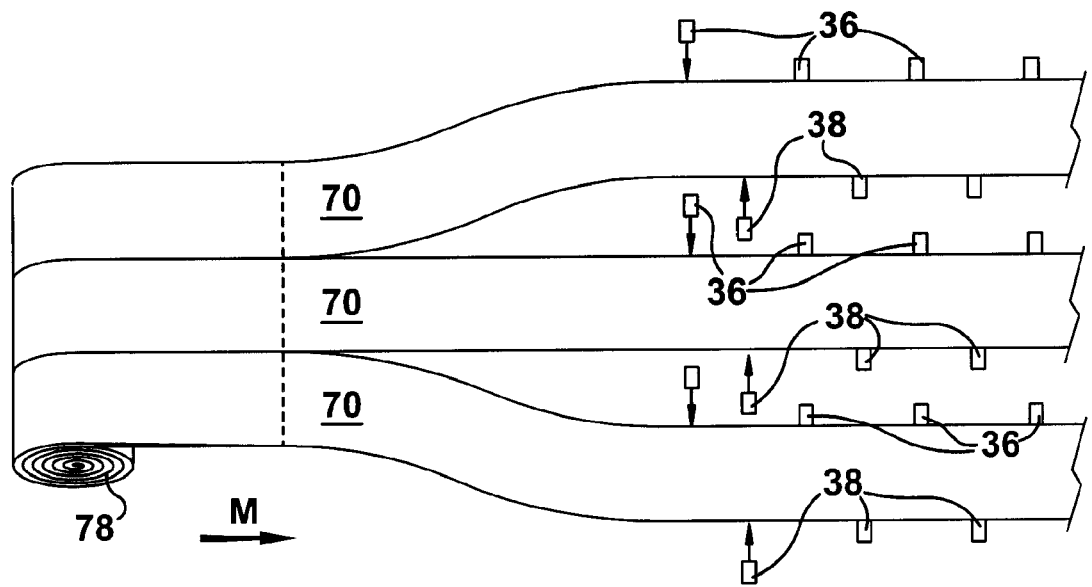
FIGS. 7A-7E are schematic views of some possible methods for making a plural number of the continuous strips.
Figure 7B:
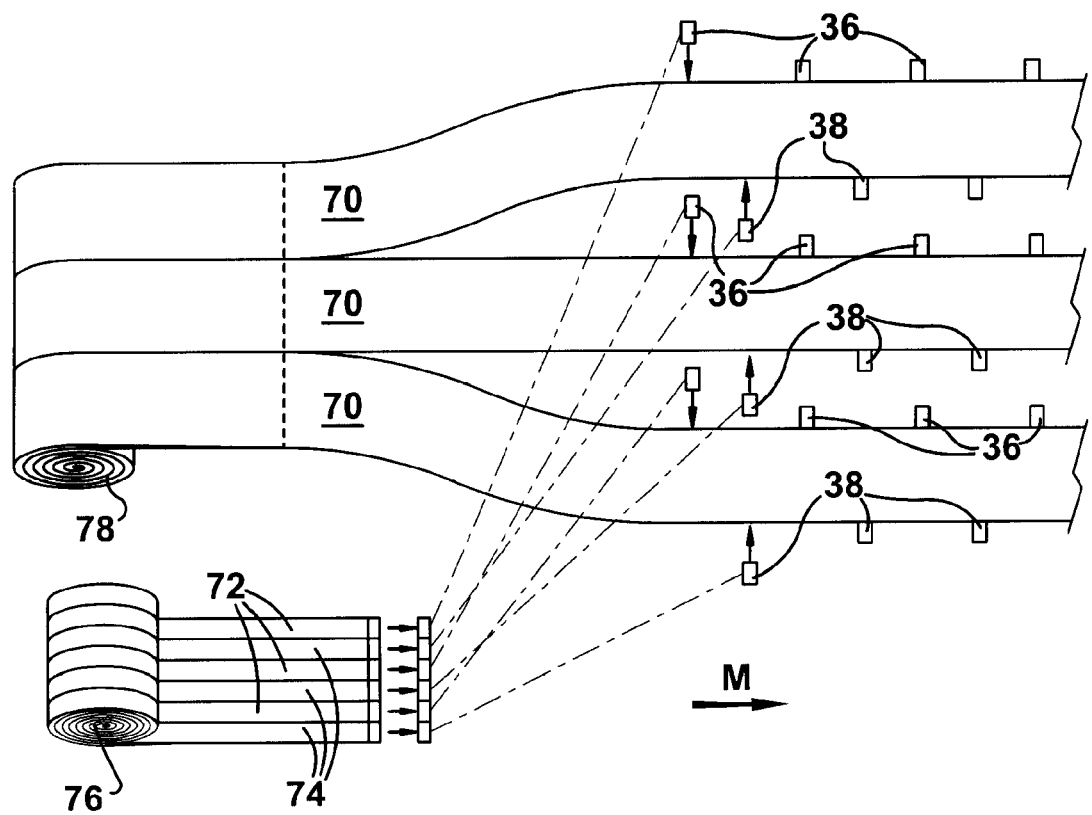
Figure 7C:
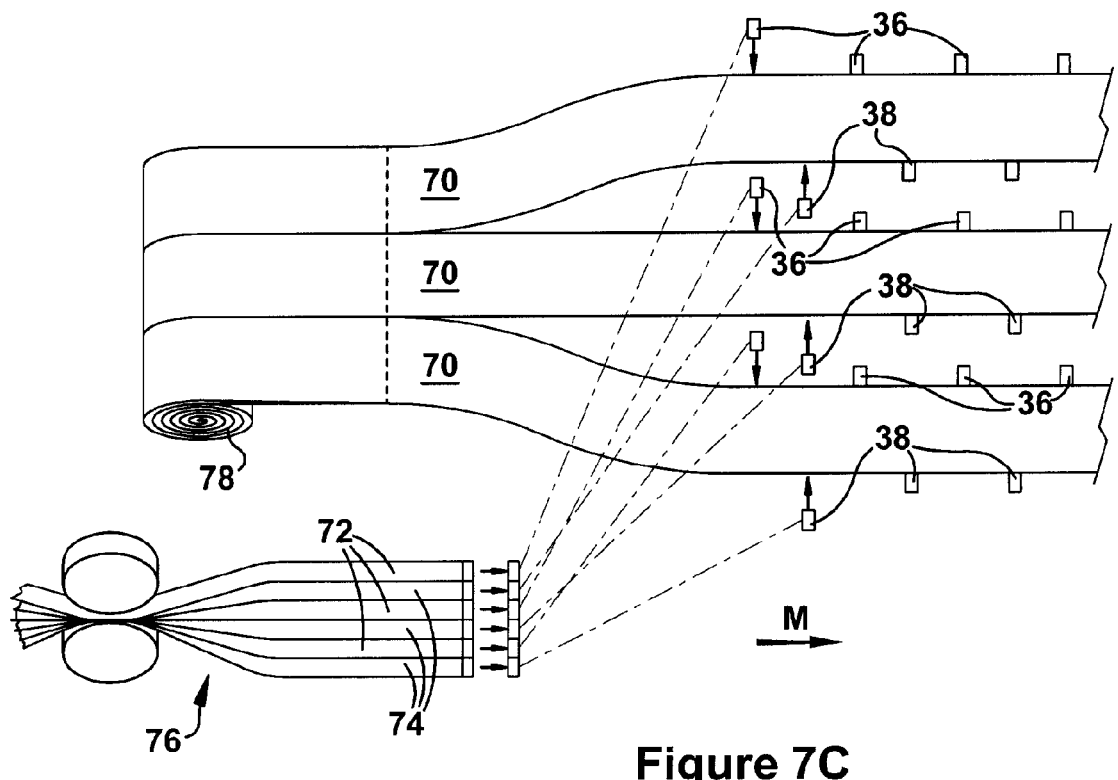

The plural number (n) sets of first fasteners 36 and the plural number (n) sets of second fasteners 38 (e.g., the three sets of first fasteners 36 and the three sets of second fasteners 38) can be supplied by six ribbons 72/74 divided in the machine direction. (FIGS. 7A-7C.) Although illustrated otherwise, the fasteners 36/38 can be folded prior to or after the anchoring steps. The six ribbons 72/74 can be split/spread from fastener stock 86. (FIG. 7B.) Formation (e.g., lamination) of the ribbons 72/74 and/or fastener stock 76 can occur in-line with the fastener-supplying and fastener-anchoring steps. (FIG. 7C.)

Figure 7D:
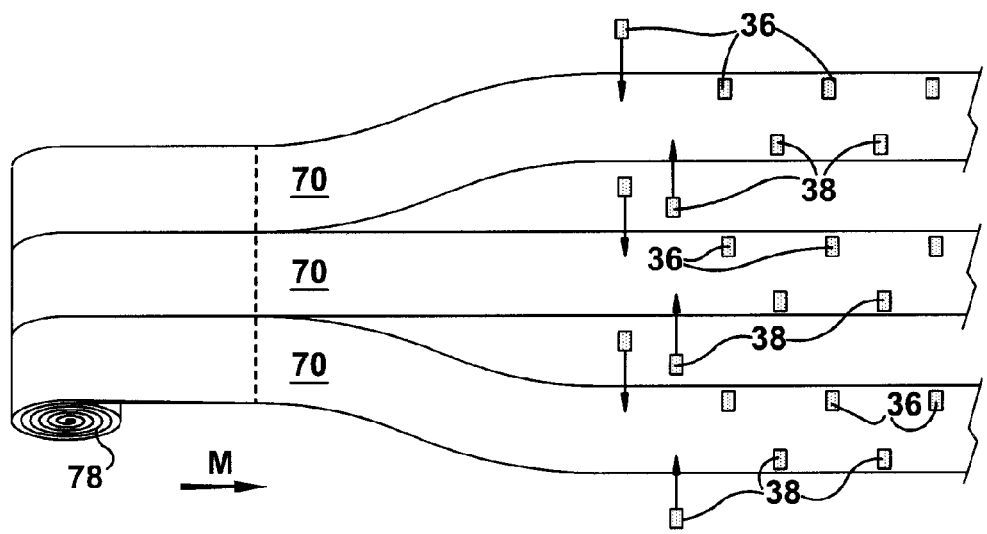
Figure 7E:
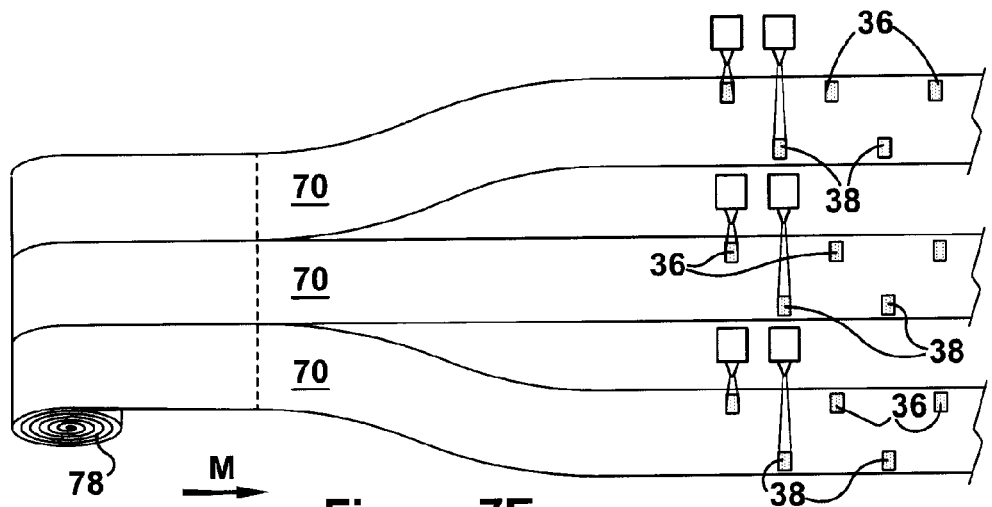

A method wherein panel stock 78 is split into a plural number (n) of webs 70 of panel material can also be employed when the fasteners 36/38 comprise discrete islands/patches. (FIGS. 7D and 7E.)

Figure 8:
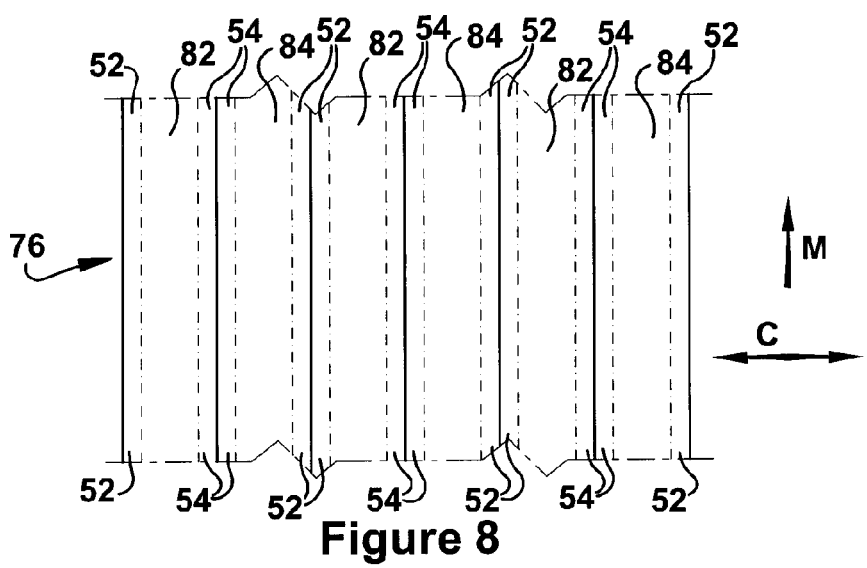
FIG. 8 is a plan view of possible fastener stock.

As was mentioned when describing the fifth and seventh series of drawings, fastener stock 76 can be split into ribbons 72/74 which are then divided into the fasteners 36/38 upstream of the anchoring steps. The fastener stock 76 can include aisles 82 and 84 corresponding to the first set of fasteners 36 and the second set of fasteners 38, respectively. (FIG. 8.) The aisles 82 and 84 can alternate across the stock 76, and pairs of adjacent aisles 82/84 can be symmetrically positioned so that their ends 52 (e.g., anchoring ends) abut against each other and their ends 54 (e.g., fingerlifts) abut against each other. This situating of the ribbons 72/74, and thus eventually the fasteners 36/38, is consistent with the respective anchoring orientations on the lateral regions 44/46. Thus, once the stock 76 is split between the aisles 82/84, turning/twisting of the ribbons 82/84 and/or fasteners 36/38 is minimized.

Figure 9:
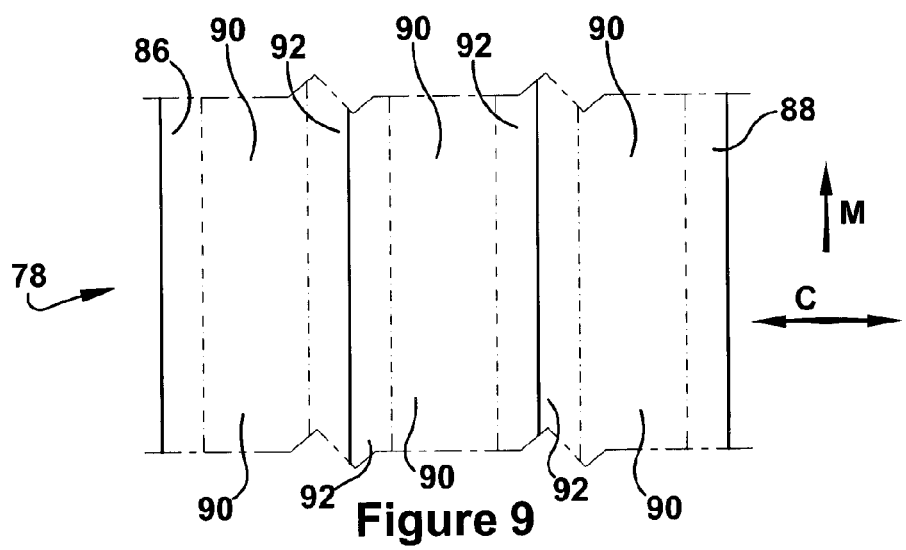
FIG. 9 is a plan view of possible panel stock.

As was mentioned when describing the seventh series of drawings, panel stock 78 can be cut into the plural number (n) of webs 70 of panel material, each web 70 having a central region 42, a first lateral region 44, and a second lateral region 46. If the regions 42/44/46 are made of different materials and/or have different properties, the panel stock 78 can comprise lanes 86/88/90/92 running continuously in the machine direction M. (FIG. 9.) The lanes can include one margin lane 86, one margin lane 88, the plural number (n) of intermediate lanes 90, and the plural number minus one (n−1) of intermediate lanes 92. Thus, in the illustrated embodiment wherein three webs 70 of panel material are provided, there are three intermediate lanes 90 and two intermediate lanes 92.

The margin lane 86 runs adjacent one longitudinal edge of the stock material 78 and corresponds to a first lateral region 44, and the margin lane 88 runs adjacent the other longitudinal edge of the stock material 78 and corresponds to a second lateral region 46. The intermediate lanes 90 correspond to the central regions 42. One lane 90 is positioned adjacent the margin lane 86, another lane 90 is positioned adjacent the margin lane 86, and the remaining (if any) lanes 90 are positioned therebetween. The intermediate lanes 92 are positioned between the lanes 90 and correspond to the combination of a second lateral region 46 and a first lateral region 44. When splitting the panel stock 78 to form the webs 70 of panel material, the split occurs at the middle of each intermediate lane 92 whereby (n−1) splits are made to produce (n) webs 70.

Referring now to FIG. 10A-10J, methods for making a plurality of the side panels 10 and the side panels 12 from the continuous strip 40 is shown. In this method, the continuous strip 40 is separated (e.g., cut) in machine direction M to form a first set of side panels 10 and a second set of side panels 12. The side panels 10 in the first set each has a fastening section 26 comprising a first lateral region 44 and a first fastener 36, and a securement section 28 comprising a second lateral region 46. The side panels 12 in the second set each has a securement section 34 comprising a first lateral region 44, and a fastening section 32 comprising a second lateral region 46 and a second fastener 38. The side panels 10 in the first set alternate with the side panels 12 in the second set in the machine direction M. Although not specifically shown in the drawings, the tape fasteners 36/38 may be folded to straddle the relevant edges prior to the separating steps.

Figure 10G:
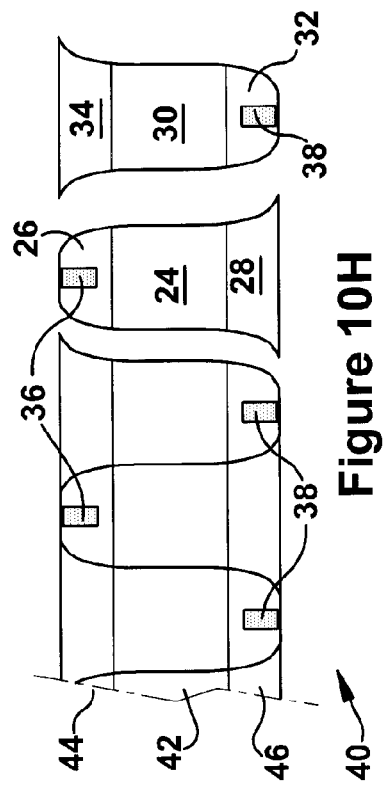
Figure 10I:
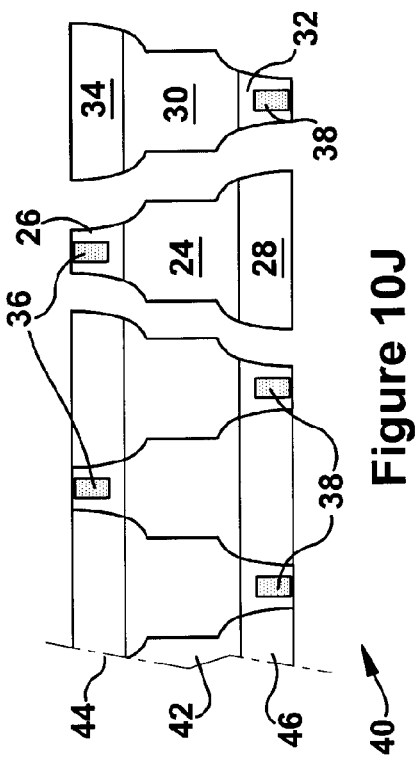
Figure 10H:
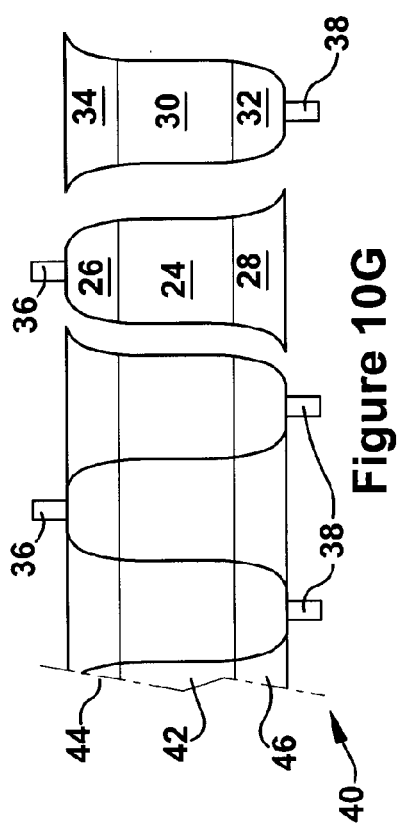
Figure 10J:
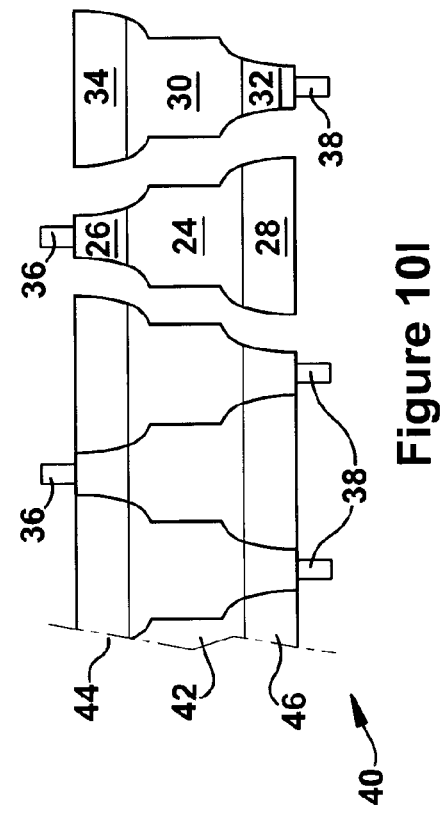

The span of each side panel 10/12 is coextensive with the width (w) of the strip 40 in the cross direction C and/or are situated in a no-waste pattern. The side panels 10 in the first set have the same geometry as the side panels 12 in the second set. The side panel shapes can have rectangular shapes (FIGS. 10A and 10B), or can have non-rectangular nesting shapes such as, for example, triangular (FIGS. 10C and 10D), trapezoidal (FIGS. 10E and 10F), sinusoidal (FIGS. 10G and 10H). The side panel shapes can additionally or alternative comprise complimentary convex/concave shapes, with or without a polygonal shape positioned therebetween. (FIGS. 10I and 10J.)

Figure 11A:
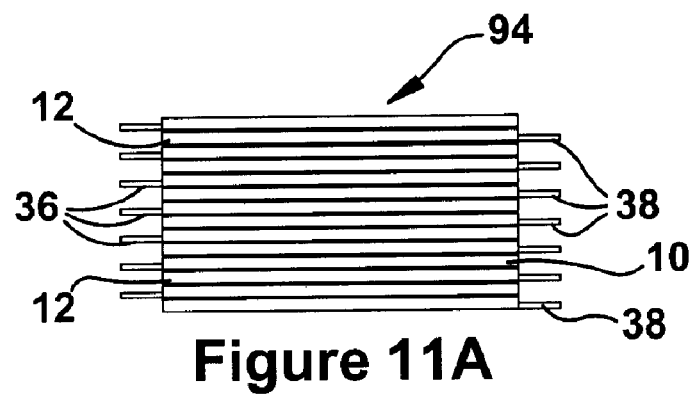
FIGS. 11A-11B are schematic views of possible formats for sequential supply of the side panels.
Figure 11B:
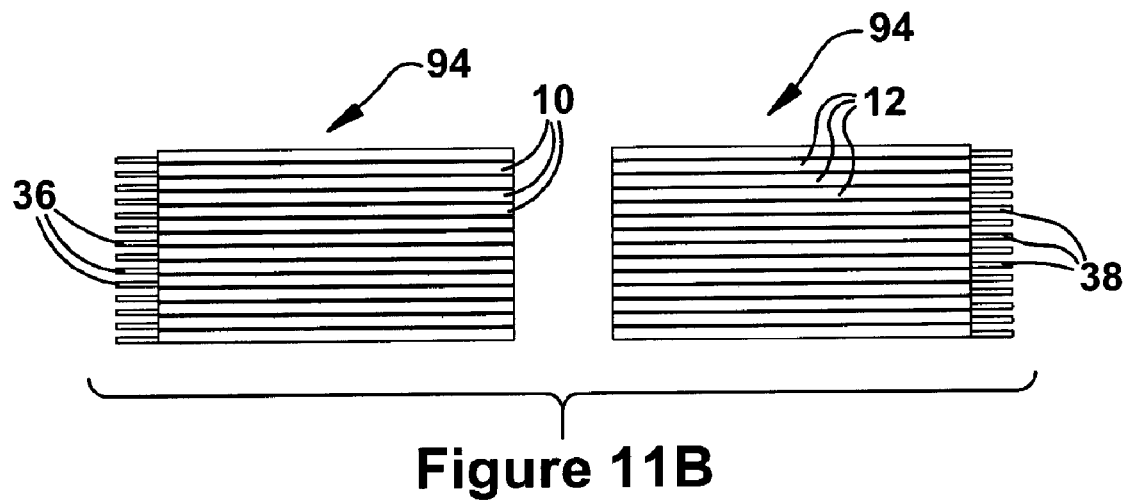
Figure 12H:
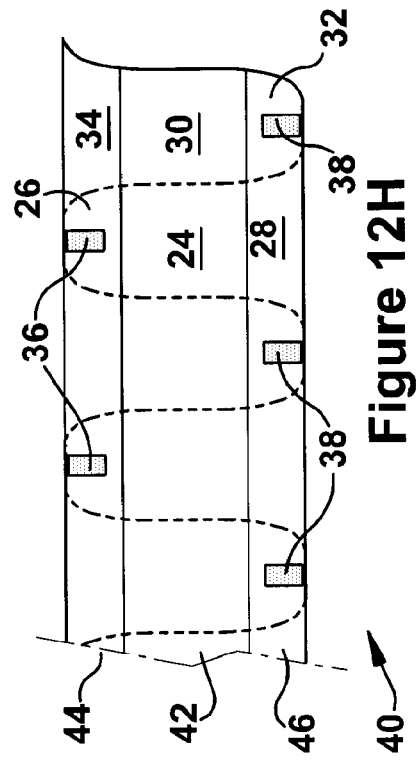
Figure 12J:
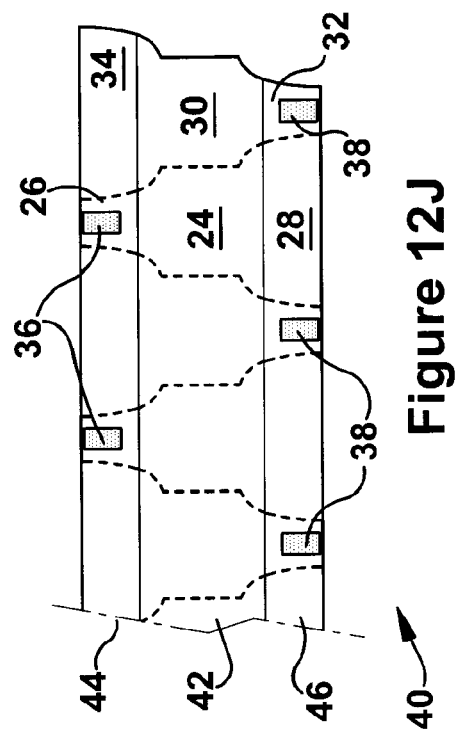
Figure 12G:
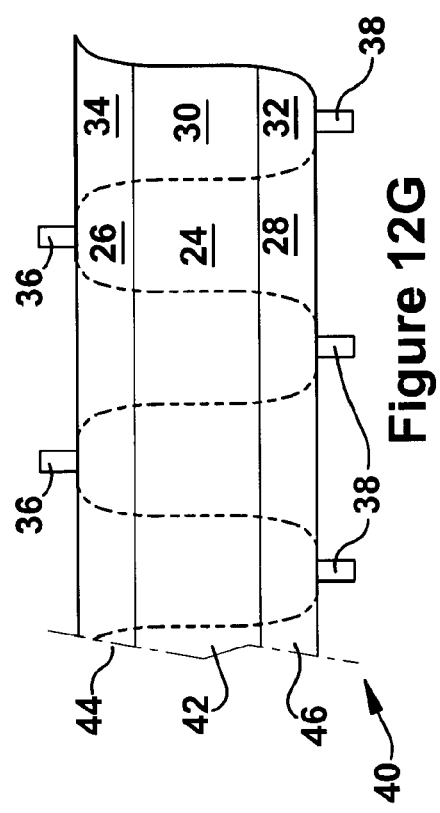
Figure 12I:
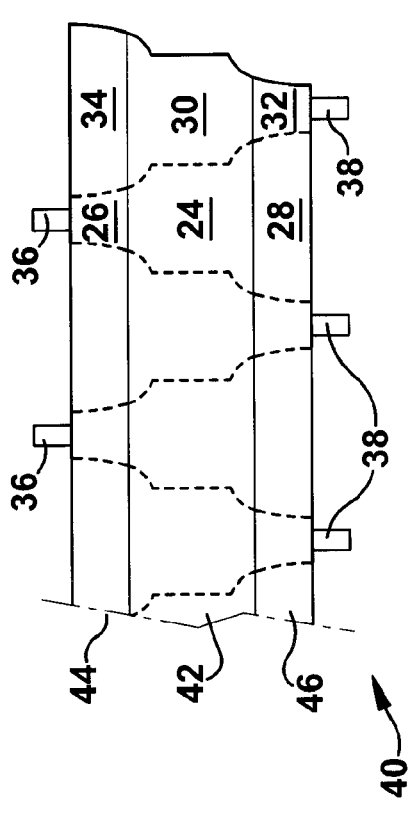

The separated side panels 10/12 can be assembled into a format 94 suitable for sequential dispensing. For example, the side panels 10 and the side panels 12 can be in a single stack in an alternating order. (FIG. 11A.) Alternatively, the side panels 10 can be placed in one stack and the side panels 12 placed in a separate stack. (FIG. 11B.) The stack(s) 94 can then stored and/or shipped to the side-panel-securement location. If, however, the side-panel-separation steps are performed in-line with the side-panel-securement steps, an assembly into the format 94 may not be necessary. Although the fasteners 36/38 are shown unfolded, and not straddling the edge of the respective lateral region 44/46, they could be folded over as in the roll/stack 80 (See FIGS. 6A and 6B).

Prior to the final separation steps shown in the eleventh series of drawings, and probably (but not necessarily) after the anchoring steps, partial separations 96 may be made in the continuous strip 40 which mirror those formed in the final separation steps. (FIGS. 12A-12E.) The partial separations can comprise discontinuous cuts or perforations, less-than-thickness indents, etc. The continuous strip 40 with such partial separations can be provided in a format 80 suitable for continuous supply (see FIGS. 6A-6D). The final separation steps can be performed by accomplished by cutting, tearing, or other suitable techniques.

Referring now to FIGS. 13A-13I, possible methods for securing the side panels 10/12 to a string of diaper chassis 16 are shown. In the illustrated methods, the side panels 10/12 have a rectangular shape and the fasteners 36/38 are each in the form of a tape assembly 50. However, the side panels 10/12 can have any of the non-rectangular shapes discussed above, or any other suitable shapes. Additionally, the fasteners 36/38 need not comprise tape assemblies 60, and can instead comprise the islands/patches 68 of hooks/adhesive discussed above, or any other suitable fasteners. If the fasteners 36/38 do comprise tape assemblies 60, they can be folded before or after the fastener-anchoring steps, the panel-separating steps, and/or the panel-securing steps.

In side-panel-securing steps, a side panel 10 is secured to the left side of each diaper chassis 16 (e.g., the left side of its rear portion 18) and a side panel 12 from the second set is secured to the right side of each diaper chassis 16 (e.g., the right side of its rear portion 18). The securement section 28 (comprising the second lateral region 46) of the side panel 10 is secured to the chassis left side and the securement section 34 (comprising the first lateral region 44) is secured to the chassis right side. The left panel's fastening section 26, comprising the first lateral region 44 and carrying the first fastener 36, projects outward from the left side of the diaper chassis 16. The right panel's fastening section 32, comprising the second lateral region 46 and carrying the second fastener 38, projects outward from the right side of the diaper chassis 16.

Figure 13A:
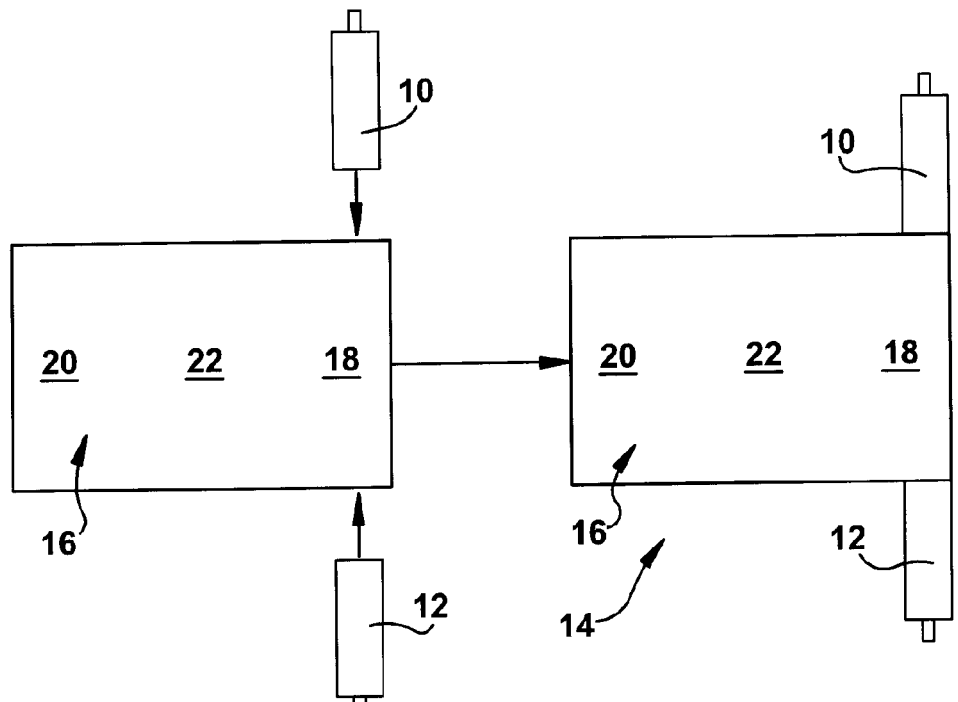
FIGS. 13A-13I are schematic views of possible methods for securing side panels to a string of diaper chassis.
Figure 13B:
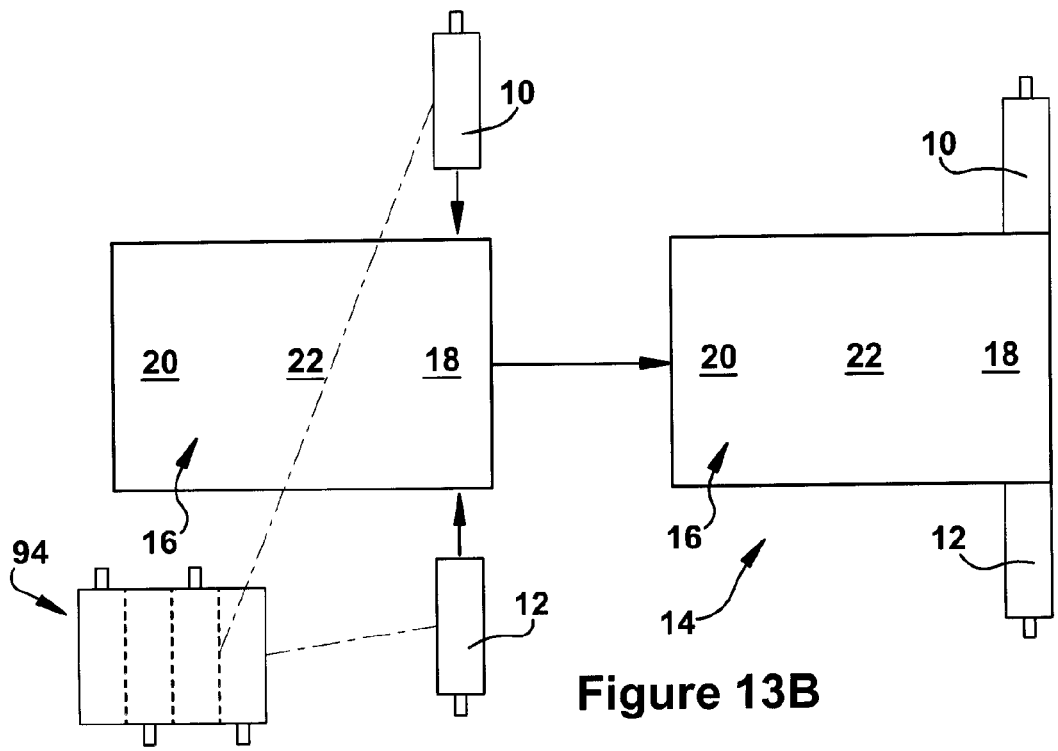
Figure 13C:
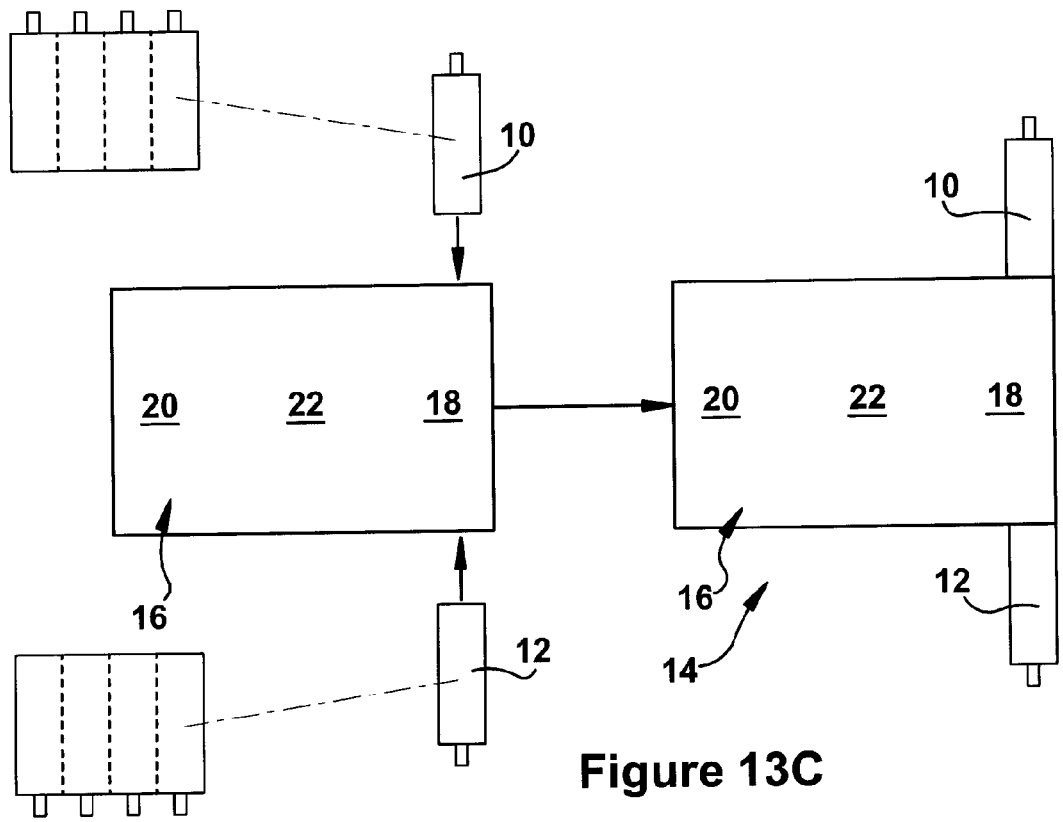

The side panels 10/12 can be made at one location (e.g., a side panel manufacturing site) and the securement steps can be performed at a remote location (e.g., the diaper manufacturing site). (FIGS. 13B and 13C.) More specifically, at one location (e.g., the side panel manufacturing site), the continuous strip 40 can be separated into side panels 10/12, assembled into the dispensing format 94 (FIGS. 11A and 11B), and then shipped or otherwise conveyed in this format to the other location (e.g., the diaper manufacturing site). At the latter location (e.g., the diaper manufacturing site), the side panels 10/12 would be dispensed from the stack(s) 94 and secured to the diaper chassis 16.

Figure 13D:
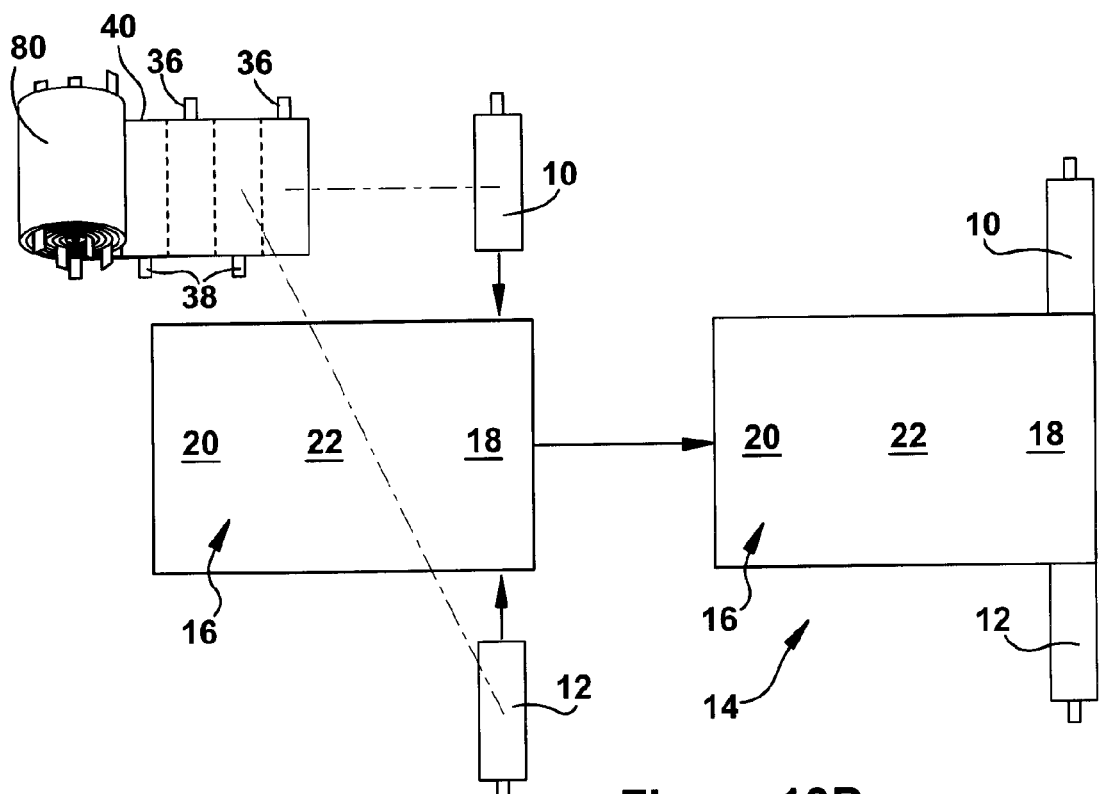
Figure 13E:
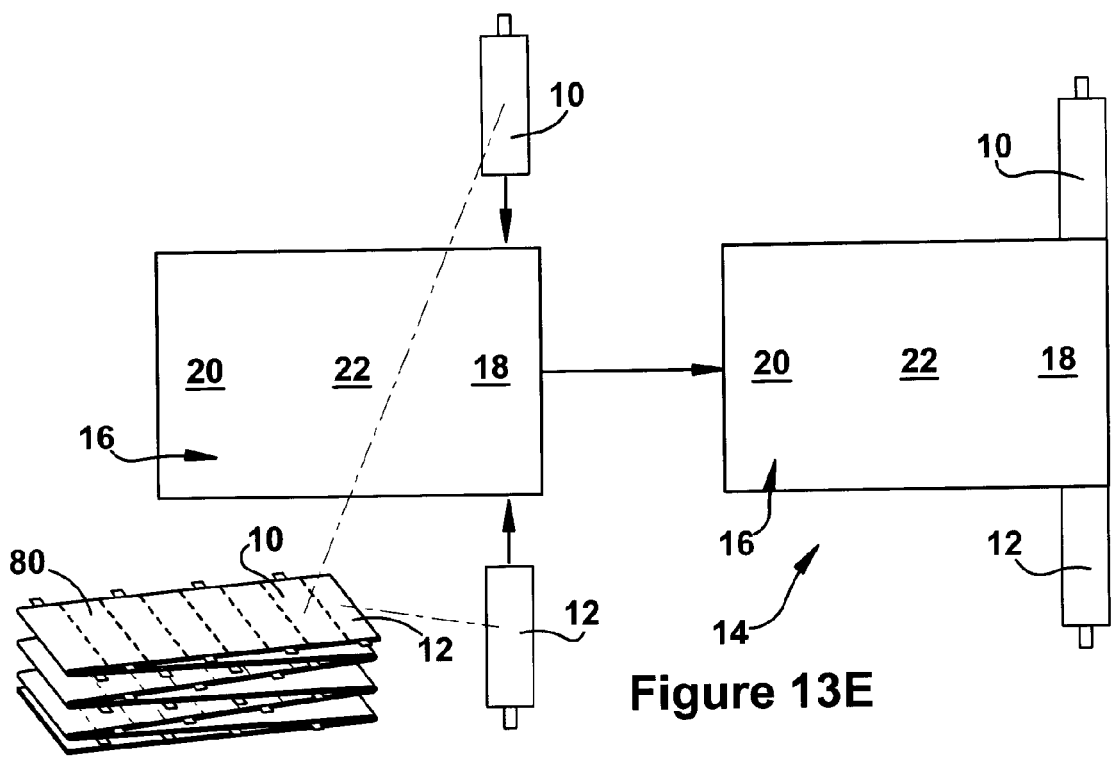

As another option, both the separating steps and securing steps can be performed at the same location (e.g., the diaper manufacturing site). (FIGS. 13D and 13E.) Specifically, for example, the continuous strip 40 can be manufactured at one location, assembled into a format 80 suitable for continuous supply, and then shipped or otherwise conveyed to the separating/securing location (e.g., the diaper manufacturer). The industry norm usually tends to favor different locations for strip-making and side-panel-securing steps. That being said, the continuous strip 40 could be manufactured at the same location (e.g., the diaper manufacturer) as the side-panel-securing steps.

Figure 13F:
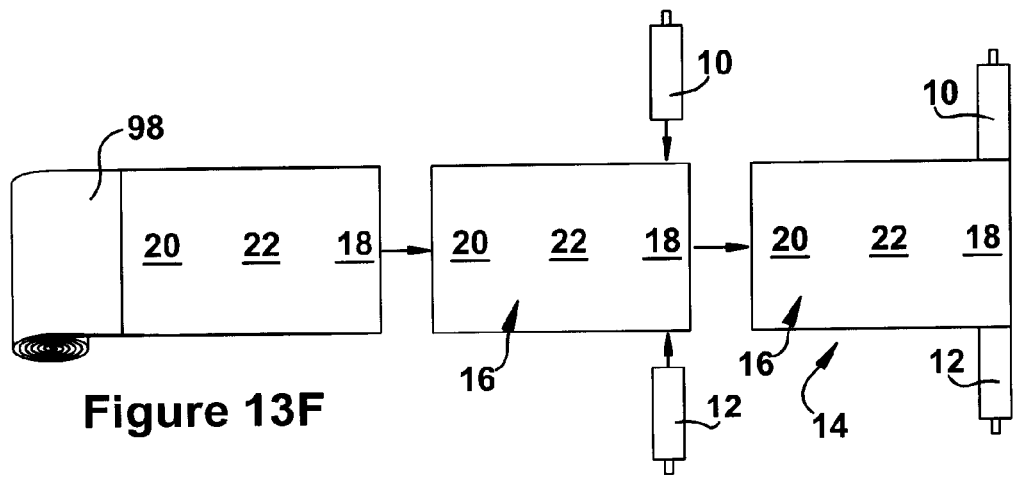
Figure 13G:
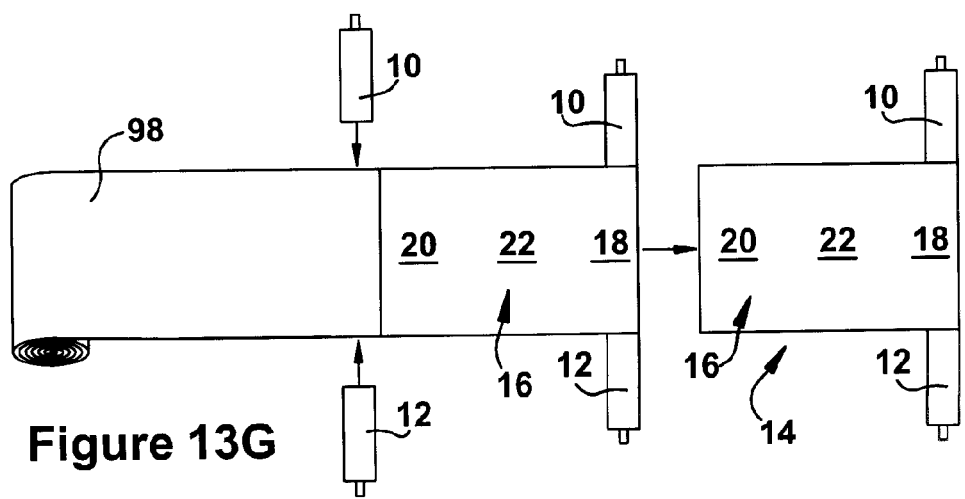
Figure 13H:
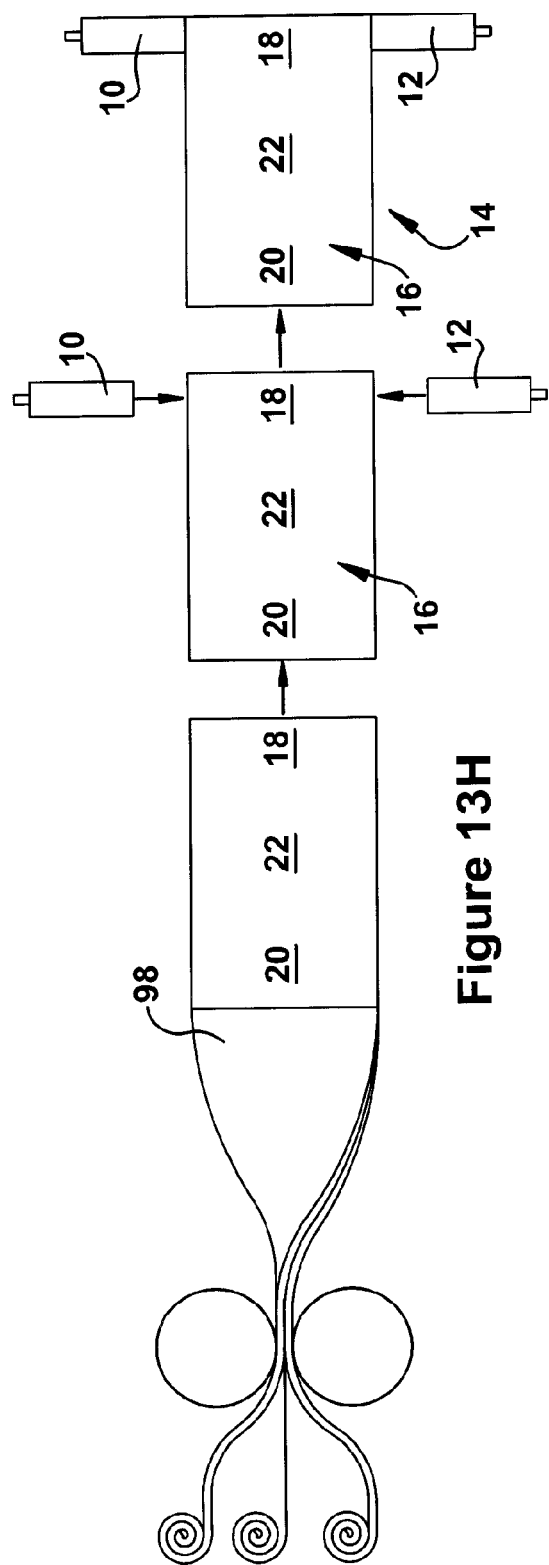
Figure 13I:
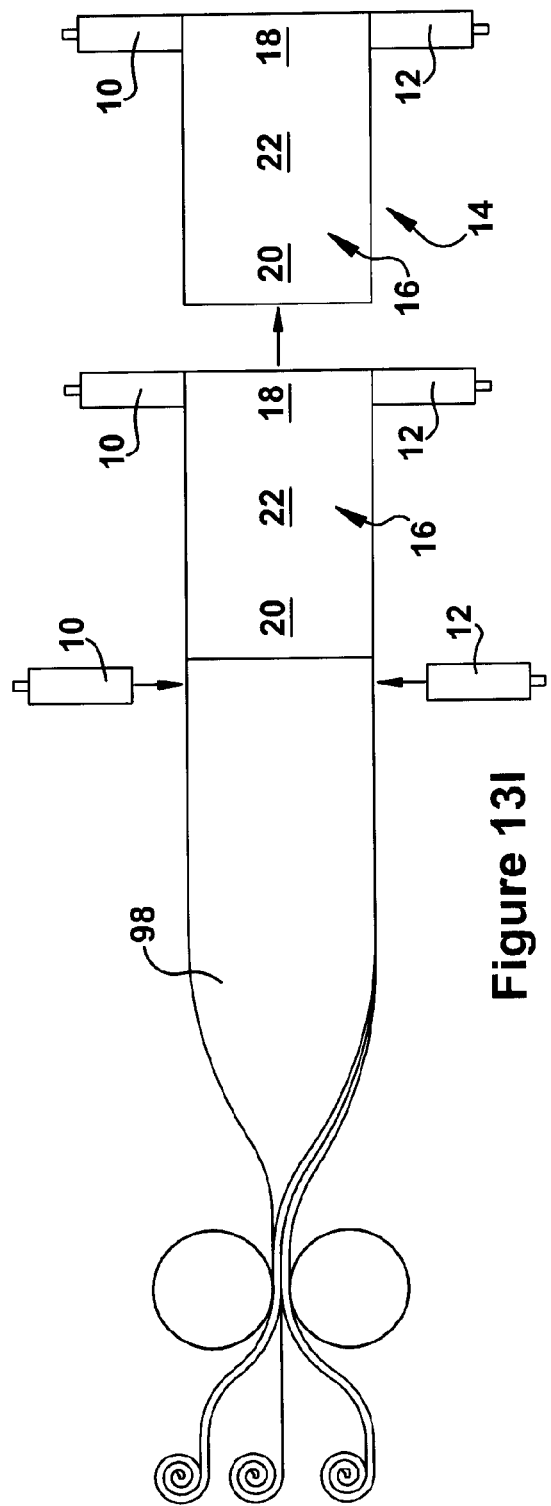

In any of the above-discussed (and/or other possible) sequences of strip-making, strip-separating, and side-panel-securing steps, the chassis 16 can be in its final form whereby securement of the side panels 10/12 essentially completes the construction of the diaper 14. Some or all of these steps can be performed in-line with the chassis-making steps. For example, a string of chassis 14 can be cut from chassis stock 98 upstream or downstream of the side-panel-securing steps. (FIGS. 13F-13H.) The chassis stock 98 can be supplied in a format suitable continuous supply (e.g., a roll) (FIG. 13F and FIG. 13G) or it can be made in-line with the chassis-cutting steps (FIG. 13H).

Although certain concepts (e.g., side panels, strips, fasteners, chassis, diapers, methods, etc.) have been shown and described with respect to some possible embodiments, it is obvious that equivalent alterations and modifications will occur to others skilled in the art upon the reading and understanding of this specification and the annexed drawings. In regard to the various functions performed by the above described elements (e.g., components, assemblies, systems, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function. In addition, while a particular feature of the invention may have been described above with respect to only one or more of several illustrated embodiments, such a feature may be combined with one or more other features of the other embodiments, as may be desired and advantageous for any given or particular application.

The invention claimed is:

1. A continuous strip for making a plurality of diaper side panels, said strip comprising a central region, a first lateral region, a second lateral region, a first set of fasteners anchored to the first lateral region, and a second set of fasteners anchored to the second lateral region;

the central region, the first lateral region, and the second lateral region each running the length of strip in the machine direction (M);

the first lateral region being located on one longitudinal side of the central region and the second lateral region being located on the other longitudinal side of the central region; and the first set of fasteners being spaced from each other in the machine direction (M), the second set for fasteners being spaced from each other in the machine direction (M);

wherein the central region is an elastic region and is made of a different material, and/or has different properties, than the lateral regions;

wherein the central region occupies between 20% and 90% of the width of the strip in the cross direction (C), with the lateral regions occupying the remaining territory on either side thereof; and wherein the fasteners are anchored to the longitudinal edge of the respective lateral region and the fasteners extend outwardly away from the central region past the longitudinal edge to which they are anchored.

2. A continuous strip as set forth in claim 1, wherein the first and second set of fasteners are staggered in the cross direction (C) relative to each other.

3. A continuous strip as set forth in claim 1, wherein the distal longitudinal edge of the first lateral region and the distal longitudinal edge of the second lateral region defines the width of the strip in the cross direction (C).

4. A continuous strip as set forth in claim 1, comprising one or more layers coextensive across the central region, the first lateral region, and the second lateral region;

and/or one or more layers non-coextensive across the central region, the first lateral region, and the second lateral region.

5. A continuous strip as set forth in claim 1, wherein the fasteners in the first set are the same as the fasteners in the second set.

6. A continuous strip for making a plurality of diaper side panels, said strip comprising a central region, a first lateral region, a second lateral region, a first set of fasteners anchored to the first lateral region, and a second set of fasteners anchored to the second lateral region.;

the central region, the first lateral region, and the second lateral region each running the length of strip in the machine direction (M);

the first lateral region being located on one longitudinal side of the central region and the second lateral region being located on the other longitudinal side of the central region; and the first set of fasteners being spaced from each other in the machine direction (M), the second set for fasteners being spaced from each other in the machine direction (M);

wherein the central region is an elastic region and is made of a different material, and/or has different properties, than the lateral regions; and wherein the central region occupies between 20% and 90% of the width of the strip in the cross direction (C), with the lateral regions occupying the remaining territory on either side thereof; and said strip further comprising partial separations dividing the strip into a first set of side panel shapes and a second set of side panel shapes, said partial separations following along a substantially linear path, the first set of side panel shapes each including a first lateral region with a first fastener anchored thereto and a second lateral region without a second fastener anchored thereto;

the second set of side panel shapes each including a first lateral region without a first fastener anchored thereto and a second lateral region with a second fastener anchored thereto;

the side panel shapes in the first set alternating with the side panel shapes in the second set in the machine direction (M), and wherein fasteners extend outwardly away from the central region past their respective longitudinal edges.

7. A continuous strip as set forth in claim 6, wherein the span of each side panel shape is coextensive with the width of the strip in the cross direction (C); wherein the side panel shapes are situated in a no-waste pattern; and wherein the side panel shapes in the first set are the same geometry as the side panel shapes in the second set.

8. A continuous strip as set forth in claim 6, wherein the substantially linear path extends substantially an entire width of the strip in the cross direction (C).

9. A continuous strip as set forth in claim 6, wherein the substantially linear path extends substantially an entire width of the strip from a first longitudinal edge of the strip to a second opposing longitudinal edge of the strip.

10. A roll of the continuous strip set forth in claim 6.

\* \* \* \* \*